United States Patent
Ueno et al.

(10) Patent No.: US 6,420,422 B1
(45) Date of Patent: Jul. 16, 2002

(54) OCULAR HYPOTENSIVE AGENTS

(75) Inventors: Ryuzo Ueno; Ryuji Ueno, both of Nishinomiya; Tomio Oda, Sanda, all of (JP)

(73) Assignee: Sucampo Pharmaceuticals, Inc., Bethesda, MD (US)

( * ) Notice: Subject to any disclaimer, the term of this patent is extended or adjusted under 35 U.S.C. 154(b) by 0 days.

(21) Appl. No.: 08/476,583

(22) Filed: Jun. 7, 1995

Related U.S. Application Data

(62) Division of application No. 08/161,449, filed on Dec. 6, 1993, which is a continuation of application No. 07/931,969, filed on Aug. 19, 1992, now abandoned, which is a continuation of application No. 07/774,750, filed on Oct. 11, 1991, now Pat. No. 5,236,907, which is a division of application No. 07/414,331, filed on Sep. 29, 1989, now abandoned, said application No. 08/161,449, is a division of application No. 07/760,269, filed on Sep. 16, 1991, now Pat. No. 5,166,178, which is a division of application No. 07/584,669, filed on Sep. 19, 1990, now Pat. No. 5,151,444, which is a continuation of application No. 07/246,059, filed on Sep. 19, 1988, now Pat. No. 5,001,153.

(30) Foreign Application Priority Data

| Sep. 18, 1987 | (JP) | 62-235890 |
|---|---|---|
| Dec. 29, 1987 | (JP) | 62-334037 |
| Oct. 1, 1988 | (JP) | 63-248720 |
| Oct. 1, 1988 | (JP) | 63-248721 |

(51) Int. Cl.$^7$ ............................................. A61K 31/455
(52) U.S. Cl. ....................................... 514/530; 514/573
(58) Field of Search ................................. 560/121, 118; 514/530, 573; 562/500

(56) References Cited

U.S. PATENT DOCUMENTS

| 4,128,713 A | 12/1978 | Schneider et al. |
|---|---|---|
| 4,131,738 A | 12/1978 | Smith |
| 4,599,353 A | 7/1986 | Bito |
| 4,824,857 A | 4/1989 | Goh |
| 4,883,819 A | 11/1989 | Bito |
| 4,952,581 A | 8/1990 | Bito |
| 5,001,153 A | 3/1991 | Ueno |

FOREIGN PATENT DOCUMENTS

| EP | 0093380 | 11/1983 |
|---|---|---|
| EP | 0170258 | 7/1986 |
| EP | 284180 | 1/1987 |
| EP | 0242580 | 10/1987 |
| EP | 0364417 | 9/1988 |
| EP | 0253094 | 11/1988 |
| EP | 0308135 | 3/1989 |
| EP | 0330511 | 8/1989 |
| EP | 0458590 | 5/1990 |
| EP | 281239 | 2/2000 |
| FR | 2110335 | 6/1972 |
| GB | 1324737 | 11/1970 |
| GB | 2209939 | 6/1989 |
| JP | 1418 | 1/2000 |
| JP | 66122 | 3/2000 |
| JP | 107927 | 4/2000 |

OTHER PUBLICATIONS

*Invest. Ophthalmol. Visual Sci.*, vol. 16, No. 12, Dec. 1977, pp. 1125–1134.
*Acta Pharmaceutica Sinica*, vol. 16, No. 5 (May 1981).
*Journal of Chromatography*, vol. 156, 1978, pp. 131–141.
*Arch. Int. Pharmacodyn*, vol. 207, 1974, pp. 131–138.
*Acta Physiol. Scand.*, vol. 66, 1966, pp. 509–510.
*Ophthalmic Res.* vol. 21, 1989, p. 428–435.
*Invest. Ophthal. & Visual Sci.* vol. 22, No. 5, May 1982.
*Exp. Eye Research*, vol. 44, 1987, pp. 835–837.
*Graefe's Arch. Clin. Exp. Ophthalmol.*, 222:139–141, 1985.
*Exp. Eye Res.* 38:181–194 (1984).

*Primary Examiner*—Robert Gerstl
(74) *Attorney, Agent, or Firm*—Sughrue Mion, PLLC

(57) ABSTRACT

The present invention relates to an ocular hypotensive composition and a composition for treatment of glaucoma which comprising an amount of 20-substituted-PGs or 20-substituted 15-keto-PGs effective as an ocular hypotensive agent; these compounds exhibit no or little side effect such as transient ocular hypertensive response, hyperemia of conjunctiva or of iris, dacryops, lema, closed eye and the like.

The present invention relates to ocular hypotensive agents which contains 13,14-dihydro-15-keto-prostagrandins, which shows no transient ocular hypertensive response that PGs usually show.

2 Claims, 1 Drawing Sheet

OCULAR HYPOTENSIVE AGENTS

RELATED APPLICATIONS

This application is a divisional of application U.S. Ser. No. 08/161,449, filed Dec. 6, 1993, which is a continuation of application Ser. No. 07/931,969, filed Aug. 19, 1992, now abandon, which is combined continuation application of U.S. Ser. No. 07/774,750, filed Oct. 11, 1991 now U.S. Pat. No. 5,236,907 (in turn a divisional application of U.S. Ser. No. 07/414,331, filed Sep. 29, 1989) and of U.S. Ser. No. 07/760,269, filed Sep. 16, 1991 now U.S. Pat. No. 5,166,178 (in turn a divisional application of U.S. Ser. No. 07/584,669, filed Sep. 19, 1990, now U.S. Pat. No. 5,151,444 which is a continuation of U.S. Ser. No. 07/246,069, filed Sep. 19, 1988, now U.S. Pat. No. 5,001,153).

BACKGROUND OF THE INVENTION

The present invention relates to ocular hypotensive agents or agents used for treatment of glaucoma which contains prostaglandins or 15-keto-prostaglandins, in which the carbon atom of the 20-position is substituted with a hydrocarbon group. Also, the present invention relates to ocular hypotensive agents which contain 13,14-dihydro-15-ketoprostaglandins.

Prostaglandins (hereinafter referred to as PGs) are the name given to the group of fatty acids which show various physiological activities and contained in human and animal tissues and organs. PGs essentially contain the prostanoic acid skeleton of the following formula:

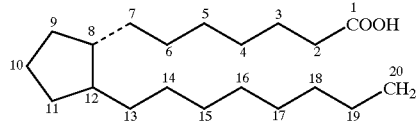

and some synthetic products may contain the above skeleton with some modification.

PGs are classified into several types according to their five-membered ring, for example,

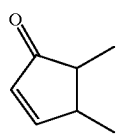

prostaglandins of the A series (PGAs):

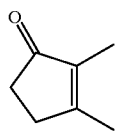

Prostaglandins of the B series (PGBs):

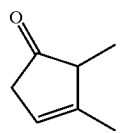

Prostaglandins of the C series (PGCs):

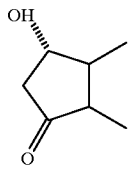

Prostaglandins of the D series (PGDs):

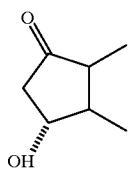

Prostaglandins of the E series (PGEs):

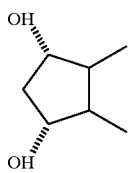

Prostaglandins of the F series (PGFs):

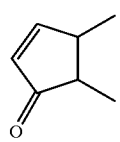

Prostaglandins of the J series (PGJs):
and the like. Further, they are classified into $PG_1$s containing 5,6-single bond:

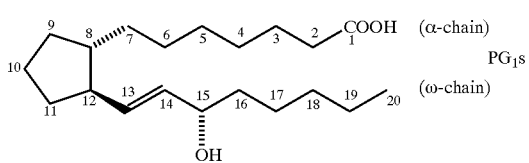

$PG_2$s containing 5,6-double bond:

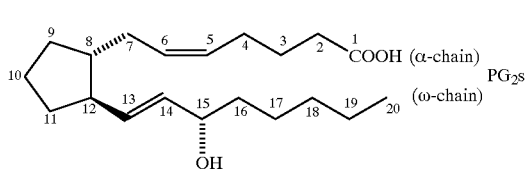

and PG₃s containing 5,6-and 17,18-double bonds:

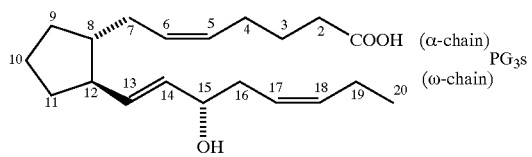

PGs are known to have various pharmacological and physiological activities, for example, vasodilation, induction of inflammation, platelet aggregation, contraction of uterine muscle, enteron contraction and the like. However, PGs also possesses various other activities, therefore there are some problems to use them as medicines. That is, when PGs are administered to obtain a single pharmaceutical activity, they often exhibit other activities as side effects. Accordingly, the investigations of PGs as a medicine have aimed to enhance the emergency of the main pharmaceutical activity. However, these investigations have been insufficient.

Among PGs, for example, PGAS, PGDS, PGEs, PGFs are known to possess ocular hypotensive potency.

For example, there is described in Japanese Patent Application KOKAI No. 1418/1984 claiming a priority based on U.S. Ser. No. 374165 (1982) by Laszlo Z. Bite that $PGF_2$ has a high ocular hypotensive activity, and 15-keto-$PGF_2$ has also it though a very little; and further in Japanese Patent Application KOKAI No. 66122/1988 claiming priorities based on three U.S. Ser. Nos. B39056 (1986), 892387(1986) and 022046 (1987) that PGA, PGB and PGC can be used for a treatment of glaucoma.

However, when topical application of these PGs, topically to rabbit eyes, they are accompanied with transient ocular hypertensive response, and still pronounced conjunctival and iridal hyperemia, and further side effects such as lacrimation, eye mucus, lid closure and the like are observed. Accordingly, there are some problems when PGs are used as remedies for glaucoma or ocular hypotensive agents.

On the other hand, PGs wherein the carbon atoms at the 13–14 positions are saturated and the carbon atom at the 15 position forms a carbonyl group are found to exist in human or animal metabolites. These 13,14-dihydro-15-keto-prostaglandins (hereinafter referred to as 13,14-dihydro-15-keto-PGs) are known to be naturally produced metabolites by enzymatic metabolism of the corresponding PGs in vivo. These 13,14-dihydro-15-keto-PGs have been reported to hardly exhibit various physiological activities that PGs possess and be pharmacologically and physiologically inactive metabolites (see, Acta Physiologica Scandinavica, 66, p.509-(1966)).

SUMMARY OF THE INVENTION

It has been found that PGs in which the number of the carbon atom in the w-chain is increased, for instance, PGs in which the carbon atom of the 20-position is substituted with a hydrocarbon group (referred to as 20-substituted PGs hereinafter) or 15-keto-PGs in which the carbon atom of the 20-position is substituted with a hydrocarbon group (referred to as 20-substituted-15-keto-PGs hereinafter) cause intraocular pressure reduction without any transient ocular hypertensive response that PGs usually show. Further, they possess enhanced ocular hypotensive potency, and exhibit ocular hypotensive effect without transient ocular hypertensive response, and with absolutely no or extremely reduced side effects such as hyperemia of conjunctiva or of iris, dacryops, lema, closed eye and the like.

It has been found the above 13,14-dihydro-15-keto PGs (metabolites) cause intraocular pressure reduction without any transient ocular hypertensive response that PGs usually show. Further, among 13,14-dihydro-15-keto-PGs, or carboxylic acid, salts, esters, compounds having a 2,3-double bond, or a 5,6-triple bond, or compounds having substituents at any of C-3, C-6, C-16, C-17, C-19 and/or C-20 positions, compounds having a lower alkyl or hydroxyalkyl group at the C-9 and/or C-11 position instead of the hydroxyl group, possess enhanced ocular hypotensive potency, and these 13,14-dihydro-15-keto-PGs may exhibit ocular hypotensive effect without transient ocular hypertensive response, and with absolutely no or extremely reduced side effects such as hyperemia. Further, we have found that these 13,14-dihydro-15-keto-PGs are accompanied with no or extremely reduced peculiar central and peripheral physiological activities which are simultaneously caused by PGs, and further they have no effects on enteron, trachea or bronchus which are characteristic of PGs.

BRIEF DESCRIPTION OF THE DRAWING

Figure 1:
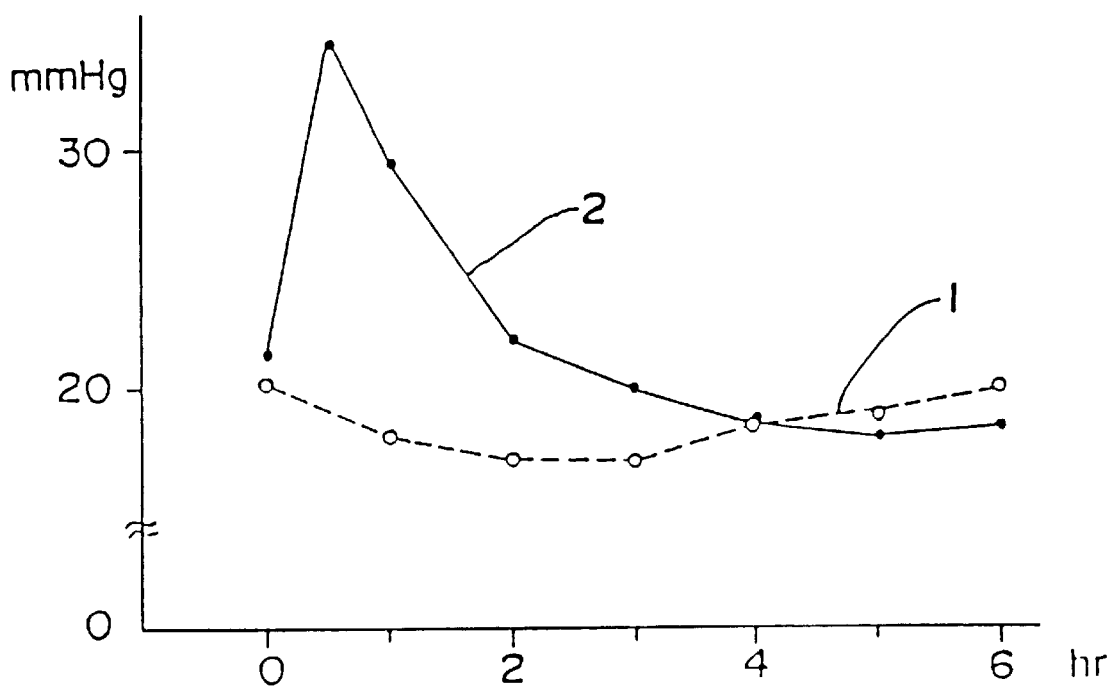

Brief Description of Drawings:

FIG. 1 is a graph showing change in intraocular pressure with time after application of prostaglandins $E_2$ to rabbits, wherein applied drugs were as follows:

(1): 13,14-dihydro-15-keto-$PGE_2$ (2): $PGE_2$

DETAILED DESCRIPTION OF THE INVENTION

The present invention provides an ocular hypotensive composition or a composition for treatment of glaucoma, which contains PGs or 15-keto-PGs, in which the carbon atom of the 20-position is substituted with a hydrocarbon group (i.e. 20-substituted-PGs or 15-keto-20-substituted-PGs) as active ingredients.

In this description, 20-substituted-PGs and 20-substituted-15-keto-PGs are expressed as follows. That is, in the both, the carbons constituting the α-chain, ω-chain and 5-membered ring are numbered according to the basic skeleton as follows:

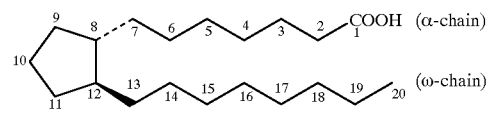

That is, in the basic skeleton, the constituent carbon atoms are numbered in such a way that the carbon atom in carboxylic acid is C-1, and the α-chain contains C-2~C-7, the number increasing toward the ring, the five-membered ring contains C-8~C-12, and the ω-chain contains C-13~C-20. When the carbons of the α-chain are fewer, the numbers of the carbons ensuing C-2 should be properly shifted, and when more than 7, the compound is named provided that the carbon at the 2 position has a substituent instead of the carboxyl group (at the 1 position) and when more than 8, the carbon atoms at the 21 position and thereafter should be regarded as a substituent. As configuration, it is considered according to that of the above essential skeleton unless otherwise described.

For example, PGD, PGE and PGF mean compounds having a hydroxyl group at the 9 and/or 11 positions. In the present intention, PGs include those having other group instead of the hydroxyl group on the 9 and/or 11 positions, they being named as 9-dehydroxy-9-substituted or 11-dehydroxy-11-substituted compounds.

20-substituted-PGs or 20-substituted-15-keto-PGs used in the present invention may be PGs wherein 20-substituted $PG_1s$ or 20-substituted-15-keto-$PG_1s$ containing a 5,6-single bond; 20-substituted-$PG_2s$ or 20-substituted-15-keto-$PG_2s$ containing a 5,6-double bond, 20-substituted-$PG_3s$ or 20-substituted-15-keto-$PG_3s$ containing both 5,6, and 17,18-double bonds may be used.

The typical examples of the PGs used in the present invention are shown below:

20-substituted or 20-substituted-15-keto-$PGA_1s$, 20-substituted or 20-substituted-15-keto-$PGA_2s$, 20-substituted or 20-substituted-15-keto-$PGA_3s$, 20-substituted or 20-substituted-15-keto-$PGB_1s$, 20-substituted or 20-substituted-15-keto-$PGB_2s$, 20-substituted or 20-substituted-15-keto-$PGB_3s$, 20-substituted or 20-substituted-15-keto-$PGC_1s$, 20-substituted or 20-substituted-15-keto-$PGC_2s$, 20-substituted or 20-substituted-15-keto-$PGC_3s$, 20-substituted or 20-substituted-15-keto-$PGD_1s$, 20-substituted or 20-substituted-15-keto-$PGD_2s$, 20-substituted or 20-substituted-15-keto-$PGD_3s$, 20-substituted or 20-substituted-15-keto-$PGE_1s$, 20-substituted or 20-substituted-15-keto-$PGE_2s$, 20-substituted or 20-substituted-15-keto-$PGE_3s$, 20-substituted or 20-substituted-15-keto-$PGF_1s$, 20-substituted or 20-substituted-15-keto-$PGF_2s$, 20-substituted or 20-substituted-15-keto-$PGF_3s$, 20-substituted or 20-substituted-15-keto-$PGJ_1s$, 20-substituted or 20-substituted-15-keto-$PGJ_2s$, 20-substituted or 20-substituted-15-keto-$PGJ_3s$ or the like. Derivatives, esters or salts of these PGs may be used, too.

These 20-substituted-PGs or 20-substituted-15-keto-PGs show strong ocular hypotensive potency without showing transient ocular hypertensive response as well as side effects such as pronounced conjunctival or iridal hyperemia, lacrimation, lid closure and the like, or extremely reduced, if any. Accordingly, these 20-substituted PGs or 20-substituted-15-keto-PGs are extremely effective as ocular hypotensive agents. Further, depending on such ocular hypotensive effect, they may be used for glaucoma therapy.

In the present invention, the ocular hypotensive effect of 20-substituted PGs or 20-substituted-15-keto-PGs may be especially remarkable in prostaglandins of the general formula:

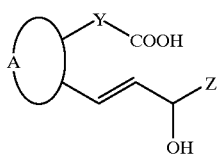

[I]

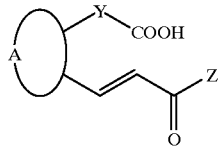

[II]

[wherein, A is

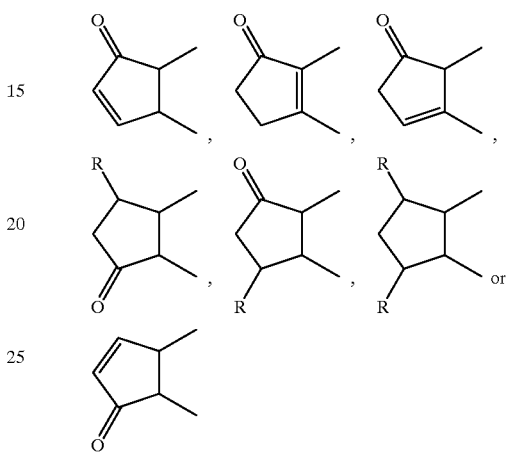

(in which R is hydroxyl, hydroxyalkyl or alkyl);

Y is a saturated or unsaturated $C_{2-6}$ hydrocarbon chain (a part of the carbon atoms constituting the hydrocarbon chain may form a carbonyl group, and the hydrocarbon chain may be substituted with one or more atoms or groups);

Z is a $C_{5-10}$ saturated or unsaturated aliphatic, alicyclic, aralkyl or aromatic hydrocarbon (the hydrocarbon may be substitued with one or more atoms or groups)] or physiologically acceptable salts derived from the general formula [I] or those having an esterified carboxyl group.

A saturated or unsaturated $C_{2-6}$ hydrocarbon chain Y includes a straight hydrocarbon chain such as an alkyl, alkenyl, alkynyl and the like. Especially, a hydrocarbon chain with 6 carbons is preferred.

The examples of an unsaturated hydrocarbon chain Y include, for example, PGs wherein carbons at the 2–3 positions or the 5–6 positions are unsaturatedly bonded.

Some of the carbons forming the hydrocarbon chain Y may form a carbonyl group. The typical example includes 6-keto-$PG_1s$ wherein the carbon at the 6 position constituting a carbonyl group.

The hydrocarbon chain Y may be substituted with one or more atoms or groups. Such atoms or groups include, for example, a halogen atom such as a fluorine, chlorine or bromine atom; an alkyl group such as methyl, ethyl; a hydroxyl group. The typical example is PGs having one or more alkyl groups at the 3 position.

The hydrocarbon group Z is a $C_5$~$C_{10}$ alkyl group, preferably $C_5$~$C_9$ alkyl group, which may have one or more branch(es). Preferable examples of the hydrocarbon group z is methyl, ethyl, n-propyl, isopropyl, n-butyl, t-butyl and the like, and most preferable one is an alkyl group having no branch.

The hydrocarbon Z may be substituted with one or more atoms or groups. Such atoms or groups include a halogen atom such as a fluorine, chlorine or bromine atom;

an alkyl group such as a methyl, ethyl, isopropyl or isopropenyl group; an alkoxy group such as a methoxy or ethoxy group; a hydroxyl group; a phenyl group; a phenoxy group and the like. The position of the substituent atom(s) or group(s) may not be limited, but typically, they may be at 16, 17, 19 and/or 20 position in the ω-chain. Particularly, compounds having one or two same or different atoms at the 16 position, for example, a halogen atom such as a fluorine atom or a substituent, for example, an alkyl group such as a methyl, ethyl, hydroxyl phenyl which may contain one or more substituents, benzyl, phenoxy, or cycloalkyl group such as a cyclopentyl or cyclohexyl group which contains the 16 position as a constituent; an alkyl group such as methyl at the 17 or 19 position: an alkyl group such as a methyl, ethyl, isopropyl, isopropenyl or alkoxy group such as a methoxy, ethoxy or propoxy group at the 20 position are preferred.

The present invention provides ocular hypotensive agents containing 13,14-dihydro-15-keto-PGs as active ingredients.

In the present invention, 13,14-dihydro-15-keto-PGs means PGs wherein carbons at the 13–14 positions are saturated and carbon at the 15 position forms a carbonyl group.

In this description, 13,14-dihydro-15-keto-PGs are expressed as follows. That is, in 13,14-dihydro-15-keto-PGs, the carbons constituting the α-chain, ω-chain and 5-membered ring are numbered according to the basic skeleton as above.

13,14-Dihydro-15-keto-PGs used in the present invention may be PGs wherein the carbon atoms at the 13–14 positions are saturated and the carbon atom at the 15 position forms a carbonyl group, and 13,14-dihydro-15-keto-$PG_1$s containing a 5,6-single bond, 13,14-dihydro-15-keto-$PG_2$s containing a 5,6-double bond, 13,14-dihydro-15-keto-$PG_3$s containing both 5,6- and 17,18-double bonds may be used.

The typical examples of the 13,14-dihydro-15-keto-PGs used in the present invention are shown below:

13,14-dihydro-15-keto-$PGA_1$s, 13,14-dihydro-15-keto-$PGA_2$s, 13,14-dihydro-15-keto-$PGA_3$s, 13,14-dihydro-15-keto-$PGB_1$s, 13,14-dihydro-15-keto-$PGB_2$s, 13,14-dihydro-15-keto-$PGB_3$s, 13,14-dihydro-15-keto-$PGC_1$s, 13,14-dihydro-15-keto-$PGC_2$s, 13,14-dihydro-15-keto-$PGC_3$s, 13,14-dihydro-15-keto-$PGD_2$s, 13,14-dihydro-15-keto-$PGD_2$S, 13,14-dihydro-15-keto-$PGD_3$s, 13,14-dihydro-15-keto-$PGE_1$s, 13,14-dihydro-15-keto-$PGE_2$s, 13,14-dihydro-15-keto-$PGE_3$S, 13,14-dihydro-15-keto-$PGF_1$s, 13,14-dihydro-15-keto-$PGF_2$s, 13,14-dihydro-15-keto-$PGF_3$s, 13,14-dihydro-15-keto-$PGJ_1$s, 13,14-dihydro-15-keto-$PGJ_2$s, 13,14-dihydro-15-keto-$PGJ_3$s or the like.

These 13,14-dihydro-15-keto-PGs show strong ocular hypotensive potency without showing transient ocular hypertensive response as well as side effects such as pronounced conjunctival or iridal hyperemia, lacrimation, lid closure and the like, or extremely reduced, if any. Accordingly, these 13,14-dihydro-15-keto-PGs are extremely effective as ocular hypotensive agents. Further, depending on such ocular hypotensive effect, they may be used for glaucoma therapy.

In the present invention, the ocular hypotensive effect of 13,14-dihydro-15-keto-PGs may be especially remarkable in prostaglandins of the general formula:

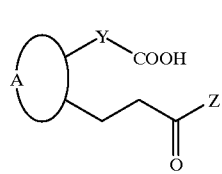

[II]

[wherein, A is

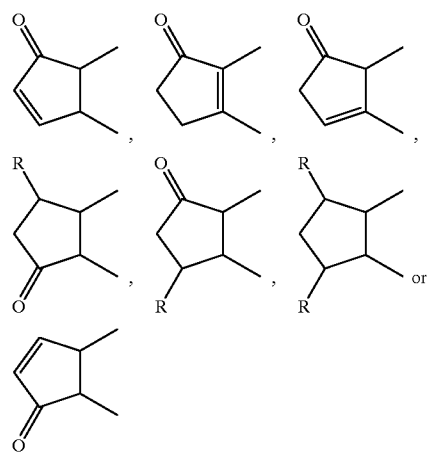

(in which R is hydroxyl, hydroxyalkyl or alkyl);

Y is a saturated or unsaturated $C_{2-6}$ hydrocarbon chain (some of the carbon atoms constituting the hydrocarbon chain may form a carbonyl group, and the hydrocarbon chain may be substituted with one or more atoms or groups);

Z is a $C_{1-10}$ saturated or unsaturated hydrocarbon forming a straight-chain, branched-chain or ring (the hydrocarbon may be substitued with atoms or groups)] or physiologically acceptable salts derived from the general formula [I] or those having an esterified carboxyl group.

A saturated or unsaturated $C_{2-6}$ hydrocarbon chain Y includes a straight hydrocarbon chain such as an alkyl, alkenyl, alkynyl and the like. Especially, a hydrocarbon chain with 6 carbons is preferred.

The examples of an unsaturated hydrocarbon chain Y include, for example, PGs wherein carbons at 2–3 positions or 5–6 positions are unsaturatedly bonded.

Some of the carbons forming the hydrocarbon chain Y may form a carbonyl group. The typical example includes 6-keto-$PG_1$s wherein the carbon at the 6 position constituting a carbonyl group.

The hydrocarbon chain Y may be substituted with one or more atoms or groups. Such atoms or groups include, for example, a halogen atom such as a fluorine, chlorine or bromine atom; an alkyl group such as methyl, ethyl; a hydroxyl group. The typical example is PGs having one or more alkyl groups at the carbon at the 3 position.

Z means a $C_{1-10}$ saturated or unsaturated hydrocarbon group. The hydrocarbon itself may form a ring or may be substituted with one or more atoms or groups.

As the hydrocarbon group Z, those with a $C_{3-9}$ straight chain are particularly preferred. Those with five carbons corresponds to the general PGs with an ω-chain having eight carbons. Accordingly, as described above, the hydrocarbon Z having more than 6 carbons are assumed to be a substituent of the carbon at the 20 position in the ω-chain (i.e., a hydrocarbon having seven carbons may be referred to as 20-ethyl-PGs).

The unsaturated bond may be at any position in Z. However, Z without an unsaturated bond is preferred. The examples of the hydrocarbon Z forming a ring include a cyclo-pentyl or cyclohexyl group wherein carbons at 16 or 17 position in the ω-chain may be constituent of the ring.

The hydrocarbon Z may be substituted with one or more atoms or groups. Such atoms or groups include a halogen atom such as a fluorine, chlorine or bromine atom; an alkyl group such as a methyl, ethyl, isopropyl or isopropenyl group; an alkoxy group such as a methoxy or ethoxy group; a hydroxyl group; a phenyl group; a phenoxy group and the like. The position of the substituent atom(s) or group(s) may not be limited, but typically, they may be at 16, 17, 19 and/or 20 position in the ω-chain. Particularly, compounds having one or two same or different atoms at the C-16 position, for example, a halogen atom such as a fluorine atom or a substituent, for example, an alkyl group such as a methyl, ethyl, hydroxyl phenyl which may contain one or more substituents, benzyl, phenoxy, or cycloalkyl group such as a cyclopentyl or cyclohexyl group which contains the C-16 position as a constituent; an alkyl group such as methyl at the C-17 or C-19 position: an alkyl group such as a methyl, ethyl, isopropyl, isopropenyl or alkoxy group such as a methoxy, ethoxy or propoxy group at the C-20 position are preferred.

PGs may include the compounds PGD, PGE, PGF which contain a hydroxyl group at the 9 and /or 11 position. In the present specification, PGs further include the compounds having a hydroxyalkyl or alkyl group instead of the hydroxyl group at the 9 and/or 11 position. Accordingly, the 20-substituted-PGs or 15-keto-PGs of the present invention include the compound of the general formula [I] or [II], wherein R is a hydroxyl, hydroxyalkyl or alkyl group. Such hydroxyalkyl group preferably include a hydroxymethyl or 1-hydroxyethyl, 2-hydroxyethyl or 1-methyl-1-hydroxyethyl group. As the alkyl group, a lower alkyl group, especially a methyl or ethyl group are preferred.

The configuration of R for the carbon at the 9 and/or 11 position may be an α, β or mixture thereof.

PGs of the present invention may be salts or those with an esterified carboxyl group. Such salts include physiologically acceptable salts, for example, those of an alkali metal such as sodium, potassium; those of an alkaline earth metal such as calcium, magnesium; those of physiologically acceptable an ammonium or amine salt such as ammonia, methylamine, dimethylamine, cyclopentylamine, benzylamine, piperidine, monoethanolamine, diethanplamine, monomethylmonoethanolamine, tromethamine, lysine, tetralkylammonium salt and the like. Such an ester includes, for a example, methyl, ethyl, propyl, butyl, isopropyl, t-butyl, 2-ethylhexyl, straight or branched-chain aikyl ester which may contain an unsaturated bond; for example, ester having an alicyclic group such as a cyclopropyl, cyclopentyl or cyclohexyl group; an ester containing an aromatic group such as a benzyl or phenyl group (wherein the aromatic group may contain one or more substituents); a hydroxyalkyl or alkoxyalkyl ester such as a hydroxyethyl, hydroxyisopropyl, polyhydroxyisopropyl, methoxyethyl, ethoxyethyl or methoxyisopropyl group; an alkylsilyl ester e.g., a trimethylsilyl or triethylsilyl ester; a tetrahydropyranyl ester.

Preferred esters include, for example, a straight or branched lower alkyl ester such as a methyl, ethyl, propyl, n-butyl, isopropyl or t-butyl ester; or a benzyl ester; a hydroxyalkyl ester such as a hydroxyethyl or hydroxyisopropyl ester.

The carboxyl group at the 1 position of 20-substituted-PGs or 15-keto-PGs of the present invention may be any of the above described groups. Among them, esters, especially the $C_{1-4}$ alkyl ester, especially isopropyl ester are preferred considering emergency of ocular hypotensive effect.

The PGs of the present invention may include the isomers of the above compounds. Examples of such isomers include keto-hemiacetal tautomers between the $C_6$-carbonyl and $C_9$-hydroxyl, or the $C_{11}$-hydroxyl and $C_{15}$-carbonyl; or optical isomers; geometrical isomers and the like.

Keto-hemiacetal tautomers between the $C_{11}$-hydroxyl group and $C_{15}$-carbonyl may be readily formed especially in 13,14-dihydro-15-keto-PGEs having electrophilic group such as a fluorine atom at the C-16 position.

The mixture of the isomers, for example, those of racemic body, tautomers of hydroxyl compound and hemiacetals may show similar effect as that shown by the respective compound.

In the present invention, especially preferred 20-substituted-PGs or 20-substituted-15-keto-PGs may contain a 5,6-single or double bond, or a carbonyl group at the 6 position carbon atom. Another preferred groups are 20-substituted or 20-substituted-15-keto-PGs wherein the carbon atom at the 16 position may be substituted with a halogen atom or an alkyl group.

In the present invention, especially preferred 13,14-dihydro-15-keto-PGs may contain a 5,6-single or double bond, or a carbonyl group at the 6 position carbon atom. Another preferred groups are 13,14-dihydro-15-keto-PGs having 20–24 carbon atoms. Still other preferred groups are 13,14-dihydro-15-keto-PGs wherein the carbon atom at the 16 position may be substituted with a halogen atom or an alkyl group, and further, 13,14-dihydro-15-keto-PGs having more than 20 carbons and an alkyl group at C-19 position.

Particularly, the compounds having a $C_{1-4}$ alkyl, for example, a methyl, ethyl, propyl or butyl group at the 20 position, that is, having a prolonged ω-chain show enhanced ocular hypotensive effect with little side effects such as hyperemia. Accordingly, such compounds are preferred.

That is, in 13,14-dihydro-15-keto-PGs used in the present invention, those having an alkyl group t the C-20 position may provide particularly preferable result, neglecting the structure of the five-membered ring, or the existence of double bond or other substituents. Particularly, those wherein the alkyl group is an ethyl (wherein the ω-chain contains a $C_{10}$ straight chain) may show the most pronounced ocular hypotensive effect, scarcely showing side effects such as hyperemia, thereby providing the most preferable product as a whole.

In the present invention, PGs are named according to the prostanoic acid skeleton. If named according to IUPAC, for example, $PGE_1$ corresponds to 7-[(1R,2R,3R)-3-hydroxy-2-[((E)-(3S)-3-hydroxy-1-octenyl]-5-oxo-cyclopentyl]-heptanoic acid; $PGE_2$, (Z)-7-[(1R,2R,3R)-3-hydroxy-2-[(E)-(3S)-3-hydroxy-1-octenyl]-5-oxo-cyclopentyl]-hept-5-enoic acid; 20-ethyl-$PGE_1$ is 7-{(1R,2R,3R)-3-hydroxy-2-[(E)-(3S)-3-hydroxy-1-decenyl]-5-oxo-cyclopentyl}-heptanoic acid, and 15-keto-20-ethyl-$PGE_1$ is 7-{(1R,2R,3R)-3-hydroxy-2-[(E)-(3S)-3-oxo-1-decenyl]-5-oxo-cyclopentyl}-heptanoic acid. $PGF_1α$ corresponds to 7-[(1R,2R,3R,5S)-3,5-dihydroxy-2-[(E)-(3S)-3-hydroxy-1-octenyl]-cyclopentyl]-heptanoic acid; $PGF_2α$, (Z)-7-[(1R, 2R,3R,5S)-3,5-dihydroxy-2-[(E)-(3S)-3-hydroxy-1-octenyl]-cyclopentyl]-5-heptenoic acid; therefore, 20-ethyl-PGF$_1$α is 7-[(1R,2R,3R,5S)-3,5-dihydroxy-2{(E)-(3S)-3-hydroxy-1-decenyl}-cyclopentyl]-heptanoic acid and 15-keto-20-ethyl-PGF$_1$α is 7-[(1R,2R,3R,5S)-3,5-dihydroxy-2{(E)-(3S)-3-oxo-1-decenyl}-cyclopentyl]-heptanoic acid. PGF$_2$α is (Z)-7-[(1R,2R,3R,5S)-3,5-dihydroxy-2{(E)-(3S)-3-hydroxy-1-octenyl}-cyclopentyl]-5-heptanoic acid and 15-keto-20-ethyl-PGF$_2$α is (Z)-7-[(1R,2R,3R,5S)-3,5-dihydroxy-2{(E)-(3S)-3-oxo-1-octenyl}-cyclopentyl]-5-heptanoic acid. Other PGs may also be named in the same way.

In the process for preparing 20-substituted-PGs:

A commercially available (–)-Corey lactone, which is used as a starting material, is subjected to Collins oxidation to give an aldehyde. The aldehyde is allowed to react with dimethyl (2-oxoalkyl)phosphonate anion which has a desirable length of alkyl group to give an α,β-unsaturated ketone (in order to obtain 20-methyl-PGs dimethyl(2-oxooctyl)-phosphonate anion is used).

The obtained α,β-unsaturated ketone was reduced using sodium borohydride to give α,β-unsaturated hydroxyl compound, the hydroxyl group of which is protected with THP (see Synthetic Chart I). The precursor of 20-substituted-PGs introduced with ω-chain obtained from the above process can be converted to 20-substituted-PGs according to a general process for production of PGs.

15-Keto-20-substituted-PGs can be prepared by reacting the carbonyl group of the α,β-unsaturated ketone obtained in the process as described in the production of 20-substituted-PGs with diols to protect it as ketal, and the p-phenylbenzoyl group is removed from the resultant to give an alcohol. The hydroxyl group of the alcohol is protected with dihydropyran to give a tetrahydropyranyl ether. In the above process a precursor of the 15-keto-20-substituted-PGs can be obtained (see Synthetic Chart II).

PGs containing a methyl group instead of a hydroxy group at the 11 position may be obtained as follows: PGA obtained by Jones oxidation of the hydroxy group at the 9 position of the 11-tosylate is allowed to react with a dimethyl copper complex to give 11-dehydroxy-11-methyl-PGE. Alternatively, an alcohol obtained after elimination of p-phenylbenzoyl group is converted to a tosylate. An unsaturated lactone obtained by DBU treatment of the tosylate is converted to a lactol. After introduction of an α-chain using Wittig reaction, the resulting alcohol (9 position) is oxidized to give PGA. PGA is allowed to react with dimethyl copper complex to give 11-dehydroxy-11-methyl-PGE. The resultant is reduced using sodium borohydride and the like to give 11-dehydroxy-11-methyl-PGF.

PGs containing a hydroxymethyl group instead of a hydroxyl group at the 11 position is obtained as follow: 11-dehydroxy-11-hydroxymethyl-PGE is obtained by a benzophenone-sensitized photoaddition of methanol to PGAs. The resultant is, for example, reduced using sodium borohydride to give 11-dehydroxy-11-hydroxymethyl-PGFs.

16-Fluoro-PGs may be obtained using a dimethyl (3-fluoro-2-oxoalkyl)phosphonate anion in the preparation of an α,β-unsaturated ketone. Similarly, 19-methyl-PGs may be obtained using a dimethyl (6-methyl-2-oxoalkyl) phosphonate anion.

The above 13,14-dihydro-15-keto-PGs of the present invention may be prepared according to the methods described, for example, in Japanese Patent Application Nos. 63-18326, 63-18327 and 63-108329. These descriptions may be included in the present invention.

In the process for preparing 13,14-dihydro-15-keto-compound:

A commercially available (–)-Corey lactone, which is used as a starting material, is subjected to Collins oxidation to give an aldehyde. The aldehyde is allowed to react with dimethyl (2-oxoalkyl)phosphonate anion to give an α,β-unsaturated ketone, and the resultant is reduced to ketone. The carbonyl group of the ketone is allowed to react with a diol to give a ketal, thereby protected, then a corresponding alcohol is obtained by elimination of the phenylbenzoyl group, and the resulting hydroxy group is protected with dihydropyran to give a tetrapyranyl ether. Thus, precursors of PGs wherein the ω-chain is 13,14-dihydro-15-keto-alkyl can be obtained.

Using the above tetrapyranyl ether as a starting material, 6-keto-PG$_1$s of the formula:

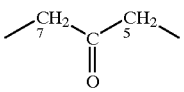

may be obtained as follows:

The tetrapyranyl ether is reduced using diisobutyl aluminium hydride and the like to give a lactol, which is allowed to react with a ylide obtained from (4-carboxybutyl) triphenylphosphonium bromide, and the resultant is subjected to esterification followed by cyclization, combining the 5,6-double bond and the C-9 hydroxyl group with NBS or iodine, providing a halide. The resultant is subjected to dehydrohalogenation with DBU and the like to give a 6-keto compound, which is subjected to Jones oxidation followed by deprotection to give the objective compound.

Further, PG$_2$s of the formula:

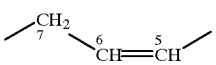

may be obtained as follows:

The above tetrapyranyl ether is reduced to the lactol, which is allowed to react with a ylide obtained from (4-carboxybutyl)triphenylphosphonium bromide to give a carboxylic acid. The resultant is subjected to esterification followed by Jones oxidation and deprotection to give the objective compound.

In order to obtain PG$_1$s of the formula:

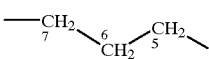

using the above tetrapyranyl ether as a starting material, in the same manner as PG$_2$ of the formula:

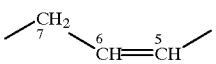

the 5,6-double bond of the resulting compound is subjected to catalytic reduction followed by deprotection.

To prepare 5,6-dehydro-PG$_2$s containing a hydrocarbon chain of the formula:

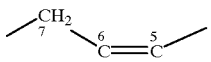

a monoalkyl copper complex or a dialkyl copper-complex of the formula:

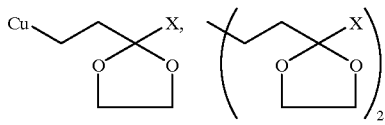

is subjected to 1,4-addition with 4R-t-butyldimethylsilyloxy-2-cyclopentyl-1-one, and the resulting copper enolate is seized with 6-carboalkoxy-1-iodo-2-hexyne or a derivative thereof.

The preparations in the present invention are not construed to be limited to them, and suitable means for protection, oxidation, reduction and the like may be employed.

The PGs of the present invention can be used as remedies for animal and human, and, in general, for systemic or local application by oral administration, intravenous injection, subcutaneous injection, suppository, collyrium, oculentum and the like. The dosage varies depending on animals, human, age, weight, conditions, therapeutic effect, administration route, treatment time and the like.

The solid composition for oral administration of the present invention includes tablets, preparations, granules and the like. In such a solid composition, one or more active ingredients may be mixed with at least, one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain-additives other than an inactive diluent, for example, a lubricant such as magnesium stearate; disintegrant such as fibrous calcium gluconate; a stabilizer such as etherified cyclodextrin, for example, $\alpha,\beta$- or $\gamma$-cyclodextrin, dimethyl-$\alpha$-, dimethyl-$\beta$-, trimethyl-$\beta$- or hydroxypropyl-$\beta$-cyclodextrin, branched cyclodextrin such as glucosyl-, maltosyl-cyclodextrin, formylated cyclodextrin, cyclodextrin containing sulfur, mitthoprotol, phospholipid and the like. When the above cyclodextrins are used, an inclusion compound with cyclodextrins may be sometimes formed to enhance stability. Alternatively, a phospholipid may be sometimes used to form a liposome, resulting in enhanced stability.

Tablets or pills may be coated with film soluble materials in the stomach or intestine such as sugar, gelatin, hydroxypropyl cellulose, hydroxypropylmethyl cellulose phthalate and the like, or with more than two layers. Further, they may be formed as capsules with absorbable substances such as gelatin.

A liquid composition for oral administration may contain a pharmaceutically acceptable emulsion, solution, suspension, syrup, elixir as well as a generally used inactive diluent, for example, purified water, ethanol and the like. Such a composition may contain, in addition to the inactive diluent, adjuvants such as wetting agents and suspensions, sweetening agents, flavoring agents, preservatives and the like.

Other compositions for oral administration include a spray formulated by known method, which may contain one or more active ingredients.

Injection for parenteral administration according to the present invention includes a steril, agueous or nonaqueous solution, suspension, emulsion and the like.

A diluent for such an aqueous solution and suspension includes, for example, injectable distilled water, physiological saline and Ringer's solution.

A diluent for non-aqueous solution and suspension includes, for example, propylene glycol, polyethylene glycol, vegetable oil such as olive oil, alcohols such as ethanol, polysorbate and the like. Such a composition may contain adjuvants such as preservatives, wetting agents, emulsifiers, dispersants, stabilizers and the like. These are sterilized, for example, by filtration through a bacteria-holding filter, compounding with germicides, gas sterilization or radio-sterilization. These may be used by preparing a sterile solid composition and dissolving in sterile water or sterile solvent for injection before use.

The collyrium according to the present invention may include a sterile aqueous or non-aqueous solution, suspension and the like. The diluent for such an aqueous solution or suspension includes, for example, distilled water or a physiological saline. The diluent for the non-aqueous solution or suspension may include an edible oil, liquid paraffin, mineral oil, propylene glycol, p-octyldodecanol and the like. Further, in order to make isotonic to tears, isotonic agents such as sodium chloride, benzalkonium chloride, phedrine chloride, procaine chloride, chloram phenicol, sodium citrate, or in order to maintain the pH value constant, buffer such as a borate or phosphate buffer may be used. Moreover, stabilizers such as sodium sulfite, sodium carbonate, EDTA, propylene glycol; thickening agents such as glycerin, carboxymethyl cellulose, carboxyvinyl polymer; diluents such as polysorbate, macrogols, aluminum monostearate; preservatives such as paraben, benzyl alcohol, sorbic acid; and further resolvents, vehicles may be compounded. These may be sterilized, for example, by the filtration through a bacteria-holding filter or heat sterilization. In the preparation of collyrium, pH value and ion strength of the agent are especially important, and they may be Optionally adjusted to the optimal value depending on the types and amounts of other active ingredients or additives used.

The oculentum according to the present invention may contain vaseline, selen 50, plastibase, macrogols as a base, and surfactant such as polysorbate, Tween, purified lanolin, jelly such as carboxymethyl cellulose, methylcellulose, carboxyvinyl polymer to enhance hydrophilism.

The ocular hypotensive agent of the present invention may be used as a remedy for glaucoma utilizing its ocular hypotensive potency. When used as the remedie for treatment of glaucoma, the present agents may be compounded with the conventional cholinergic ocular hypotensive agent (e.g., pilocarpine, carbachol, which possesses excellent miotic activity) anticholinesterases (e.g., demecarium, D.F.P., echothiophate), physostigmine salicylate, pilocarpine hydrochloride as miotics, mannitol, glycerin, isosorbide as hyperosmotic. agent for intravenous injection, chlorobutanol, benzalkonium chloride, propylparabene, methylparaben, ethylparaben, butylparaben as preservatives for collyrium, penicillin, sulfonamide, chloramphenicol, cortisone, chlorpheniramine for prevention and treatment of other inflammation.

The present invention will be illustrated in the following examples.

EXAMPLE 1

Preparations of 20-Substituted-PGs; see Synthetic Chart I 1-1) Preparation of (1S,5R,6R,7R)-6-(3-oxo-(E)-1-decenyl)-7-(4-phenylbenzoyloxy)-2-oxabicyclo[3.3.0]octane-3-one (3):

Commercially available (−)-Corey lactone (1) (7.0 g) was subjected to Collins oxidation in dichloromethane to give aldehyde (2). The aldehyde (2) was reacted with anion obtained from dimethyl (2-oxononyl)phosphonate (4.97 g) to give the title compound (3). Yield: 5.71 g 1-2) Preparation of (1S,5R,6R,7R)-6-[3(S)-hydroxy-(E)-1-decenyl]-7-(4-phenylbenzoyloxy)-2-oxabicyclo[3.3.0]octane-3-one (4a):

The unsaturated ketone (3) (3.03 g) was dissolved into a mixed solvent of methanol (60 ml) and THF (7 ml). Into the obtained solution cerium (III) chloride.7H$_2$O (2.38 g) was added at −20° C., and stirred at the same temperature for 10 minutes, into which sodium borohydride (0.25 g) was added and stirred for 5 minutes. A crude compound obtained by a usual work-up was purified using a column chromatography to give the title compound (4a) as a compound having a lower polarity and the 3R-hydroxy compound (4b) of the title compound (4a) as a compound having a higher polarity. Yield: 4.58 9 (4a:3S-hydroxy compound)

1-3) Preparation of (1S,5R,6R,7R)-7-(4-phenylbenzoyloxy)-6-[3(S)-(2-tetrahydropyranyloxy)-(E)-1-decenyl]-2-oxabicyclo[3.3.0]octane-3-one (5):

The 3S-hydroxy compound (4a) (4.58 g) was dissolved into methylene chloride (100 ml), and reacted with dihydropyran in the presence of a catalytic amount of p-toluenesulfonic acid-1H$_2$O. After a usual work-up, the reaction mixture was column-chromatographed to give the title compound (5). Yield: 5.03 g 1-4) Preparation of (1S,5R,6R,7R)-7-hydroxy-6-[3(S)-(2-tetrahydropyranyloxy)-(E)-1-decenyl]-2-oxabicyclo[3.3.0]octane-3-one (6):

The tetrahydropyranyl ether (5) (5.03 9) was dissolved into a dry methanol (300 ml), into which potassium carbonate (1.49 g ) was added, and stirred at room temperature for 6 hours. A crude compound obtained by a usual work-up was column-chromatographed to give the title compound (6). Yield: 3.25 g 1-5) Preparation of (1S,2RS,5R,6R,7R)-3,7-dihydroxy-6-[3(S)-(2-tetrahydropyranyloxy)-(E)-1-decenyl]-2-oxabicyclo[3.3.0]octane (7):

Alcohol (6) (2.00 g) was reduced in dry toluene (40 ml) using DIBAL-H at −70° C. The lactol (7) was obtained by a usual work up.

1-6) Preparation of 20-Ethyl-15S-(2-tetrahydropyranyloxy)-PGF$_2\alpha$ (B):

In dimethyl sulfoxide the lactol (7) was reacted with an ylide prepared from (4carboxybutyl)triphenyl-phosphonium bromide (8.33 g). The title compound(s) was obtained by a usual work-up.

1-7) Preparation of 20-Ethyl-15S-(2-tetrahydropyranyloxy)-PGF$_2\alpha$ Isopropyl Ester (9):

Carboxylic acid (8) was dissolved in acetonitrile (50 ml), into which DBU (1.1 g) and isopropyl iodide (2.5 g) were added. The mixture was stirred at 45° C. for 5 hours. A crude compound obtained by a usual work-up was column-chromatographed to give the title compound (9). Yield: 1.00 g 1-8) Preparation of 11R-(t-butyldimethylsiloxy)-20-ethyl-15S-(2-tetrahydropyranyloxy)-PGF$_2\alpha$ Isopropyl Ester (10):

The isopropyl ester (9) (0.37 g) was dissolved into dry DMF (3 ml), and reacted with imidazole (0.059 g) and t-butyldimethylsilyl chloride (0.132 g). A crude compound obtained by a usual work-up was purified by a column chromatography to give the title compound (10). Yield: 0.26 g 1-9) Preparation of 11R-(t-butyldimethylsiloxy)-20-ethyl-15S-(2-tetrahydropyranyloxy)-PGE$_2$ Isopropyl Ester (11):

The 11-silyl ether (10) (0.303 9) in acetone (20 ml) was oxidized using Jones reagent at −40° C. to give the title compound (11). Yield: 0.27 g 1-10) Preparation of 20-ethyl-PGE$_2$ Isopropyl Ester (12) and 20-ethyl-PGA$_2$ Isopropyl Ester (13):

11R-(t-butyldimethylsiloxy)-20-ethyl-15S-(2-tetrahydropyranyloxy)-PGE$_2$ isopropyl ester (11) (0.27 9) was stirred in a mixed solvent of acetic acid/water (7/1) (20 ml) at 65° C. for 15 hours. A crude product obtained by a concentration under reduced pressure was column-chromatographed to give the title compound (12) as a colorless oily compound (higher polarity) and the title compound (13) as a colorless oily compound (lower polarity). Yield of 20-ethyl-PGE$_2$ isopropyl ester (12) and 20-ethyl-PGA$_2$ isopropyl ester (13) are 0.040 g and 0.080 g respectively.

1-11) Preparation of 20-ethyl-PGF$_2\alpha$ Isopropyl Ester (14):

The 20-ethyl-15S-(2-tetrahydropyranyloxy)-PGF$_2\alpha$ isopropyl ester (9) (0.60 g) was dissolved in a mixed solvent of acetic acid/water/THF (3/1/1) (20 ml), and maintained at 40–45° C. for 3 hours. A crude product obtained by the concentration under reduced pressure was column-chromatographed to give the title compound (14) as a colorless solid material. Yield: 0.023 g The $^1$H NMR and Mass spectra of the 20-ethyl-PGF$_2\alpha$ isopropyl ester are shown hereinafter:
$^1$H NMR(CDCl$_3$) δ: 0.86(3H,t,J=6 Hz), 1.18(6H,d,J=7 Hz), 1.10–2.60(26H,m), 3.17(1H,m), 3.70–4.23(3H,m), 4.95(1H,hept,J=7 Hz), 5.20–5.60(4H,m)
Mass(EI) m/z 424(M$^+$), 406(M$^+$−H$_2$O), 388(M$^+$−2H$_2$O), 370(M$^+$−3H$_2$O)

The $^1$H NMR and Mass spectra of the 20-ethyl-PGE$_2$ isopropyl ester are shown hereinafter:
$^1$H NMR(CDCl$_2$) δ: 0.88(3H,t,J=5 Hz), 1.23(6H,d,J=7 Hz), 1.04–2.90(25H,m), 3.11(1H,m), 3.85–4.23(2H,m), 4.96(1H,hept,J=7 Hz), 5.33(2H,m), 5.58(2H,m)
Mass(EI) m/z 422(M$^+$), 404(M$^+$−H$_2$O), 386(M$^{+-}$2H$_2$O), 345(M$^+$−H$_2$O-iC$_3$H$_7$O)

The $^1$H NMR and Mass Spectra of 20-ethyl-PGA$_2$ isopropyl ester are shown hereinafter:
$^1$H NMR(CDCl$_2$) δ: 0.73–1.05(3H,m), 1.21(6H,d,J=6 Hz), 1.03–2.70(22H,m), 3.19(1H,m), 4.05(1H,m), 4.96(1H, hept,J=6 Hz), 5.36(2H,m), 5.56(2H,m), 6.14(1H,d,J=6 Hz), 7.46(1H,dd,J=6 Hz,J=2.5 Hz)
Mass(EI) m/z 404(M$^+$), 386(M$^+$−H$_2$O), 345(M$^+$-i-C$_3$H$_2$O), 327(M$^{+-H}$$_2$O-i-C$_3$H$_7$O)

The $^1$H NMR spectra were recorded on HITACHI R-90H (available from K. K. Hitachi Seisaku-sho) using heavy chloroform as a solvent.

Mass spectrography was measured by Mass spectrometer M-80B (available from K. K. Hitachi Seisaku-sho) with a direct inlet system at 70 eV of ionizing potential.

EXAMPLE 2

Preparation of 15-Keto-20-substituted-PGs

1. Preparation of 15-Keto-20-ethyl-PGF$_2\alpha$-isopropyl Ester (10') (see Synthetic Chart II)

1-1) Preparation of (1S,5R,6R,7R)-6-(3-oxo-(E)-1-decenyl)-7-(4-phenylbenzoyloxy)-2-oxabicyclo[3.3.0]octane-3-one (3'):

Commercially available (−)-Corey lactone (1) (7 g) was subjected to Collins oxidation in dichloromethane to give aldehyde (2'). The aldehyde (2') was reacted with dimethyl (2-oxononyl)phosphonate (4.97 g) anion to give the title compound (3').

1-2) Preparation of (1S,5R,6R,7R)-6-[3,3-ethyleneoxy-(E)-1-decenyl]-7-(4-phenylbenzoyloxy)-2-oxabicyclo[3.3.0]octane-3-one (4'):

The unsaturated ketone (3') (2.0 g) obtained in the above process was refluxed overnight with ethylene glycol (12 g) in benzene (100 ml) in the presence of a catalytic amount of p-toluene sulfonic acid-1H$_2$O while removing the generating water. The reaction mixture was chromatographed (hexane/ethyl acetate=2/1–1/1) to give the title compound (4'). Yield: 1.98 g 1-3) Preparation of (1S,5R,6R,7R)-6-[3,3-ethylenedioxy-(E)-1-decenyl]-7-hydroxy-2-oxabicyclo[3.3.0]octane-3-one (5'):

The ketal (4') (1.98 g) was treated with potassium carbonate (0.6 g) in methanol (50 ml) to give the title alcohol (5'). Yield: 1.12 g 1-4) Preparation of (1S,5R,6R,7R)-6-[3,3-ethylenedioxy-(E)-1-decenyl]-7-(2-tetrahydropyranyloxy)-2-oxabicyclo[3.3.0]octane (6'):

The alcohol (5') obtained in the above process (1-3) (0.88 g) was reacted with dihydropyran in the presence of a catalytic amount of pyridium p-toluenesulfonate in methylene chloride (50 ml) to give the title compound tetrahydropyranyl ether (6'). Yield: 1.07 g 1-5) Preparation of (1S,2RS,5R,6R,7R)-6-[3,3-ethylenedioxy-(E)-1-decenyl]-2-hydroxy-7-(2-tetrahydropyranyloxy)-2-oxabicyclo[3.3.0]octane (7'):

The tetrahydropyranyl ether (6') (1.07) was reduced using DIBAL-H in toluene (20 ml) at −70° C. The resultant was worked up according to a usual manner to give the title compound lactol (7').

1-6) Preparation of 15,15-Ethylenedioxy-20-ethyl-11R-(2-tetrahydropyranyloxy)-PGF$_2\alpha$ (8'):

The lactol (7') was reacted with an ylide prepared from (4-carboxybutyl)triphenylphosphonium bromide (4.5 g) and sodium hydride in dimethyl sulfoxide at room temperature. According a usual work-up the title compound carboxylic acid (8') was obtained.

1-7) Preparation of 15,15-Ethylenedioxy-20-ethyl-1R-(2-tetrahydropyranyloxy)-PGF$_2\alpha$ Isopropyl Ester (9'):

The title compound isopropyl ester (9') was prepared by esterifying the carboxylic acid (8') using isopropyl iodide and DBU in acetonitrile (20 ml). Yield: 1.0 g 1-8) Preparation of 15-Keto-20-ethyl-PGF$_2\alpha$ Isopropyl Ester (10'):

15,15-ethylenedioxy-20-ethyl-11R-(2-tetrapyranyloxy)-PGF$_2\alpha$ isopropyl ester (9) (0.195 g) was added into a mixed solvent of acetic acid/THF/water (3/1/1) (15 ml), and held at 40–50° C. for 3 hours. A crude compound obtained by the concentration of the reaction mixture under reduced pressure was chromatographed to give the title compound (10') as a colorless oily product. Yield: 0.142 g The $^1$H NMR and Mass spectra of the title compound (10') is as follow:

$^1$H NMR (CDCl$_2$) δ: 0.87(3H,t,J=6 Hz), 1.10(6H,d,J=7 Hz), 1.05–2.65(26H,m), 4.05(1H,m), 4.19(1H,m), 4.96(1H, hept,J=6 Hz), 5.34(2H,m), 6.12(1H,d,J=16 Hz), 6.65(1H,dd, J=16 Hz,J=9 Hz)

Mass(EI) m/z 422(M$^+$), 404(M$^+$−H$_2$O), 386(M$^+$−2H$_2$O), 360, 345

(2) Preparation of 15-keto-20-ethyl-PGE$_2$ Isopropyl Ester (12')

2-1) 15,15-ethylenedioxy-20-ethyl-11R-(2-tetrahydropyranyloxy)-PGE$_2$ Isopropyl Ester (11'):

The compound (9') obtained by the above process (1-7) (0.311 g) was oxidized with Jones reagent at −40° C. in acetone (15 ml) to give the title compound (11'). Yield: 0.245 g 2-2) Preparation of 15-Keto-20-ethyl-PGE$_2$ Isopropyl Ester (12'):

The compound (11') (0.240 g) was added to a mixed solvent of acetic acid/THF/water (3/1/1) (15 ml), and held at 35–45° C. for 2 hours. A crude compound obtained by the concentration of the resultant under reduced pressure was chromatographed to give the title compound (12') as a colorless oily product. Yield: 0.148 g The $^1$H NMR and Mass spectra of the obtained 15-keto-20-ethyl-PGE$_2$ isopropyl ester (12') are as follows:

$^1$H NMR(CDCl$_2$) δ: 0.87(3H,t,J=6 Hz), 1.20(6H,d,J=6 Hz), 1.03–2.95(25H,m), 4.01–4.38(1H,m), 4.94(1H,hept, J=6 Hz), 5.32(2H,m), 6.21(1H,d,J=16HZ), 6.71(1H,dd,J=16 Hz,J=8 Hz)

Mass(EI) m/z 420(M$^+$), 402(M$^+$−H$_2$O), 343(M$^+$−H$_2$O-i-C$_3$H$_7$)

(3) Preparation of 15-Keto-20-ethyl-PGA$_2$ Isopropyl ester (23') (see Synthetic Chart III)

3-1) Preparation of (1S,5R,6R,7R)-6-[3(S)-hydroxy-(E)-1-decenyl]-7-(4-phenylbenzoyloxy)-2-oxabicyclo[3.3.0]octane-3-one (13'):

Into a mixed solvent of dry THF (7 ml) and dry methanol (60 ml) was dissolved the α,β-unsaturated ketone (3') (3.03 g), to which cerium chloride (2.38 g) was added. The mixture was stirred at −20° C. for 10 minutes, and sodium borohydride (0.249 g) was added, and stirred for 5 minutes. The resultant was treated with a usual work-up, and then the obtained crude compound was chromatographed to give 3S-hydroxylcompound (1.18 g) and mixture of 3S- and 3R-hydroxyl compound (1.39 g).

The mixture of 3S-hydroxyl compound and 3R-hydroxyl compound (1.39 g) was oxidized with Jones reagent to recover an α,β-unsaturated ketone (3'), which was subjected to a reduction process again. This process was repeated to give 3S-hydroxyl compound (13') 4.58 g (total).

3-2) Preparation of (1S,5R,6R,7R)-7-(4-phenylbenzoyloxy)-6-[3(S)-(2-tetrahydropyranyloxy)-(E)-1-decenyl]-2-oxabicyclo[3.3.0]octane-3-one (14'):

The alcohol (13') (4.58 9) was treated with dihydropyran in dry methylene dichloride (100 ml) in the presence of a catalytic amount of p-toluene sulfonic acid-1H$_2$O to give the title compound tetrahydropyranyl ether (14'). Yield: 5.03 g 3-3) Preparation of (1S,5R,6R,7R)-7-hydroxy-6-[3(S)-(2-tetrahydropyranyloxy)-(E)-1-decenyl]-2-oxabicyclo[3.3.0]octane-3-one (15'):

The tetrahydropyranyl ether (14') (5.03 g) was stirred with potassium carbonate (1.49 g) in dry methanol (300 ml) at room temperature for 6 hours to give the title compound (15'). Yield: 3.25 g 3-4) Preparation of (1S,5R,6R,7R)-2,7-dihydroxy-6-[3(S)-(2-tetrahydropyranyloxy)-(E)-1-decenyl]-2-oxabicyclo[3.3.0]octane (16')

The alcohol (15') was reduced using DIBAL-H at −78° C. in toluene (60 ml) to give the title compound lactol (16')

3-5) Preparation of 15S-(2-tetrahydropyranyl-oxy)-20-ethyl-PGF$_2\alpha$ (17'):

The lactol (16') was reacted with an ylide prepared from (4-carboxybutyl)triphenyl phosphonium bromide (13.5 g) and sodium hydride in dimethyl sulfoxide at room temperature over night. According to a usual work-up the title compound (17') was obtained. Yield: 4.53 g 3-6) Preparation of 15S-(2-tetrahydropyranyl-oxy)-20-ethyl-PGF$_2\alpha$ Isopropyl Ester (18'):

The obtained carboxylic acid (17') (2.8 9) was esterified with isopropyl iodide (2.5 g) and DBU (1.1 g) in acetonitrile (50 ml) at 45° C. for 5 hours to give the title compound isopropyl ester (18'). Yield: 1.0 g 3-7) Preparation of 15S-(2-tetrahydropyranyl-oxy)-20-ethyl-11R-(t-butyldimethylsilyloxy)-PGF$_2\alpha$ Isopropyl Ester (19'):

The diol (18') (0.37 g) obtained in the process (3-6) treated with t-butyldimethylsilyl chloride (0.132 g) and imidazole (0.0594 g) in DMF (3 ml) to give the title compound silyl ether (19'). Yield: 0.26 g 3-8) Preparation of 15S-(2-tetrahydropyranyl-oxy)-20-ethyl-11R-(t-butyldimethylsilyloxy)-PGE$_2\alpha$ Isopropyl Ester (20'):

The silyl ether (19') (0.302 g) was oxidized using Jones reagent at −40—−35° C. in acetone (20 ml) to give the title compound (20'). Yield: 0.27 g 3-9) Preparation of 20-ethyl-PGA$_2$ Isopropyl Ester (22') and 20-ethyl-PGE$_2$ Isopropyl Ester (21'):

The compound (20') (0.27 g) obtained in the process of (3–8) was dissolved in acetic acid 70% solution (23 ml), and kept at 65° C. for 15 hours. A crude product obtained by the concentration of the resultant under a reduced pressure was chromatographed to give the compound (22') (Yield: 0.080 g) and the compound (21') (0.040 g).

3-10) Preparation of 15-Keto-20-ethyl-PGA$_2$ Isopropyl Ester (23'):

The obtained compound (22') (0.025 g) was oxidized with Jones reagent at −40—−35° C. in acetone (5 ml) to give the title compound (23'). Yield: 0.023 g The $^1$H NMR spectrum of the 15-keto-20-ethyl-PGA$_2$ isopropyl ester (23') is as follow:

$^1$H NMR(CDCl$_2$) δ: 0.87(3H,t,J=5.5 Hz), 1.22(6H,d,J=7 Hz), 1.03–2.75(25H,m), 3.35(1H,m), 4.96(1H,hept,J=7 Hz), 5.37(2H,m), 6.12(1H,d,J=16 Hz), 6.23(1H,dd,J=6 Hz), 6.69 (1H,dd,J=16 Hz,J=7.5 Hz), 7.46(1H,dd,J=6 Hz,J=2.5 Hz)

The $^1$H NMR spectra were recorded on HITACHI R-90H (available from K. K. Hitachi Seisakusho) using heavy chloroform as a solvent.

Mass spectrography was measured by Mass spectrometer M-80B (available from K. K. Hitachi Seisaku-sho) with a direct inlet system at 70 eV of ionized potential.

EXAMPLE 3
(Evaluation of Intraocular Pressure and Hyperemia)

For the purpose of tonometry, Japanese White male rabbits (2.0–3.0 Kg) were fixed in rabbit holders. After topical anesthetization with 0.4% oxybuprocaine hydrochloride, intraocular pressure was measured using a pneumatic applanation tonometer (manufactured by Japan Alcon). After the topical application of 50 μl of the suspensions of the test drugs in a physiological saline to one eye, the intraocular pressure was measured and the intraocular pressure reduction (%) caused by each test drug was calculated. At the same time, the extent of conjunctival hyperemia was observed. The results are shown in Table 1.

The extent of conjunctival hyperemia:

−: none

+−: barely visible hyperemia

+: slight hyperemia

++: moderate hyperemia

+++: severe hyperemia

TABLE 1

| Test Drug | Dose (μg/eye) | Percentage of Change of IOP | Hyperemia |
|---|---|---|---|
| 1 | 25 | 27 | + |
| 2 | 25 | 37 | ++ |
| 3 | 25 | 10 | +− |
| 4 | 25 | 15 | +− |
| 5 | 25 | 20 | +− |
| 6 | 25 | 30 | + |
| 7 | 25 | 10 | − |
| 8 | 25 | — | − |
| 9 | 25 | — | − |
| 10 | 100 | 46 | +++* |
| 11 | 25 | 31 | +++* |
| 12 | 10 | 32 | +++* |

*: lid-closing and severe hyperemia are observed.

Test Drug 1. 20-ethyl-PGF$_2\alpha$ isopropyl ester
2. 20-ethyl-PGE$_2$ isopropyl ester
3. 20-ethyl-PGA$_2$ isopropyl ester
4. 15-keto-20-ethyl-PGF$_2\alpha$
5. 15-keto-20-ethyl-PGF$_2\alpha$ isopropyl ester
6. 15-keto-20-ethyl-PGE$_2$ isopropyl ester
7. 15-keto-20-ethyl-PGA$_2$ isopropyl ester
8. 15-keto-PGF$_2\alpha$
9. 15-keto-PGE$_2$
10. PGF$_2\alpha$
11. PGF$_2\alpha$ isopropyl ester
12. PGE$_2$ Synthetic Chart I-1

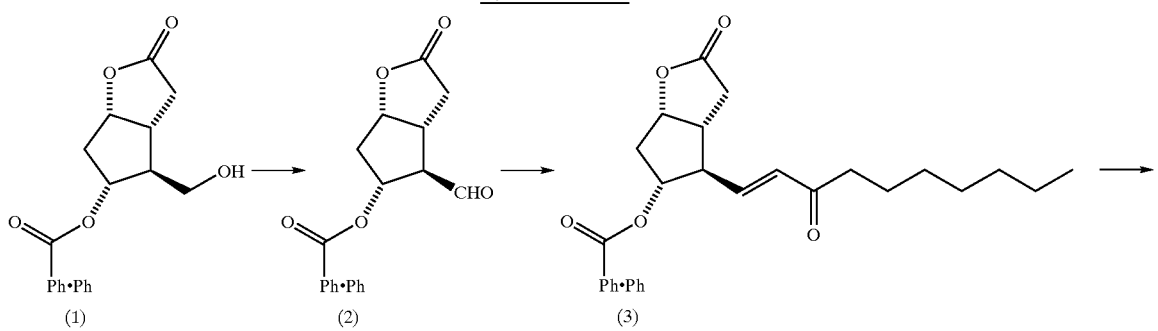

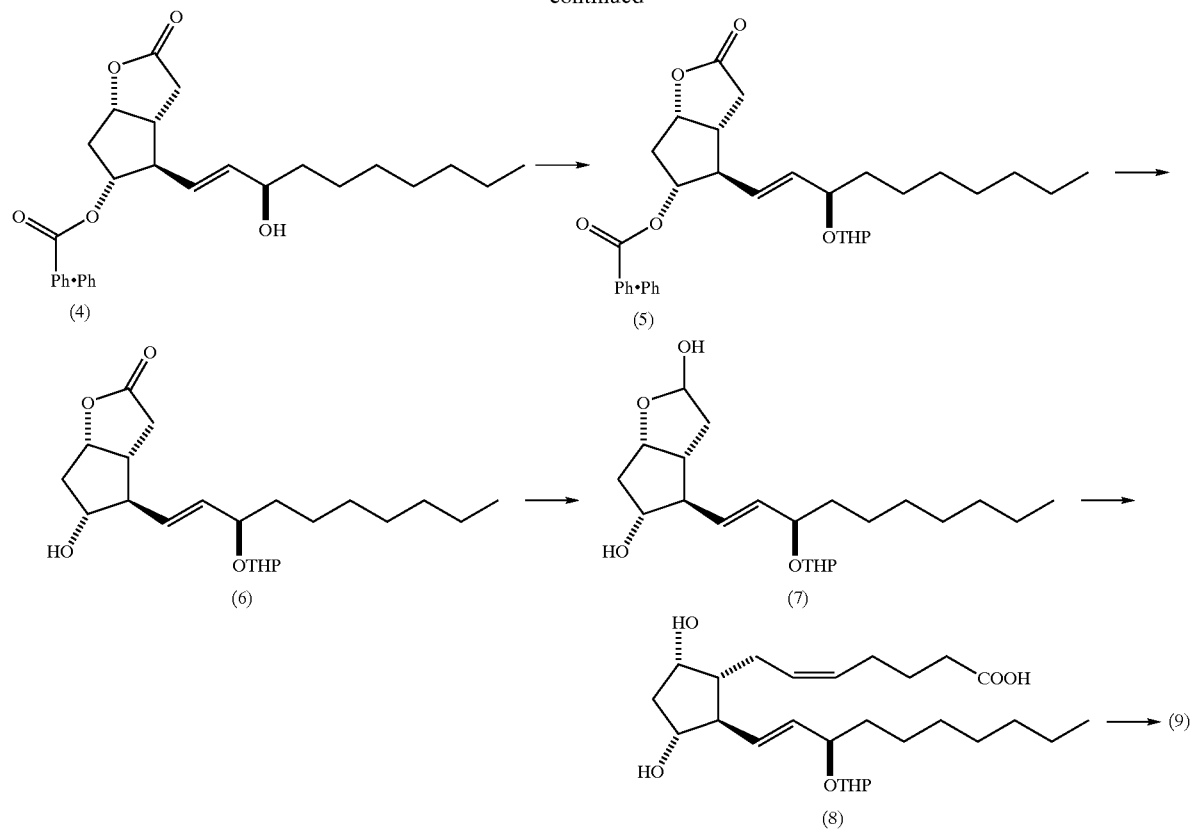
-continued
Synthetic Chart I-2
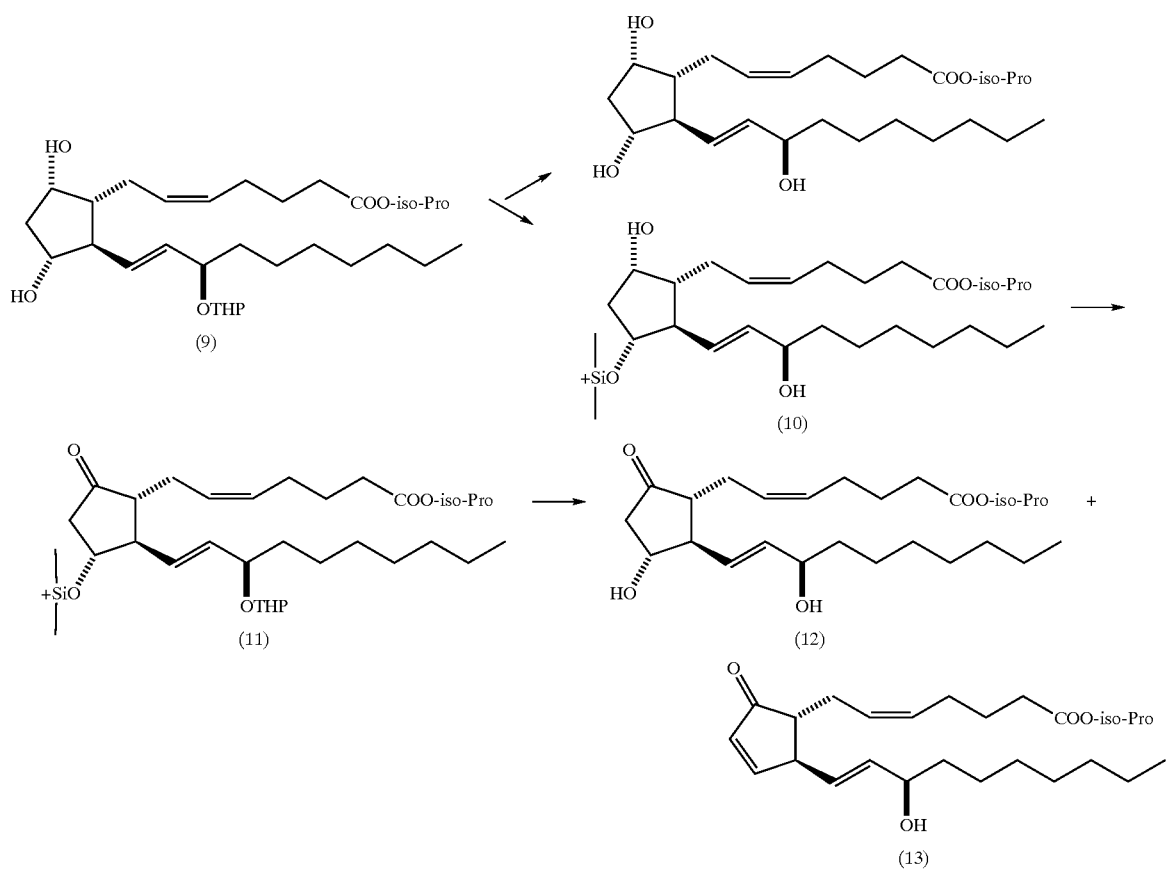

-continued
Synthetic Chart II-1
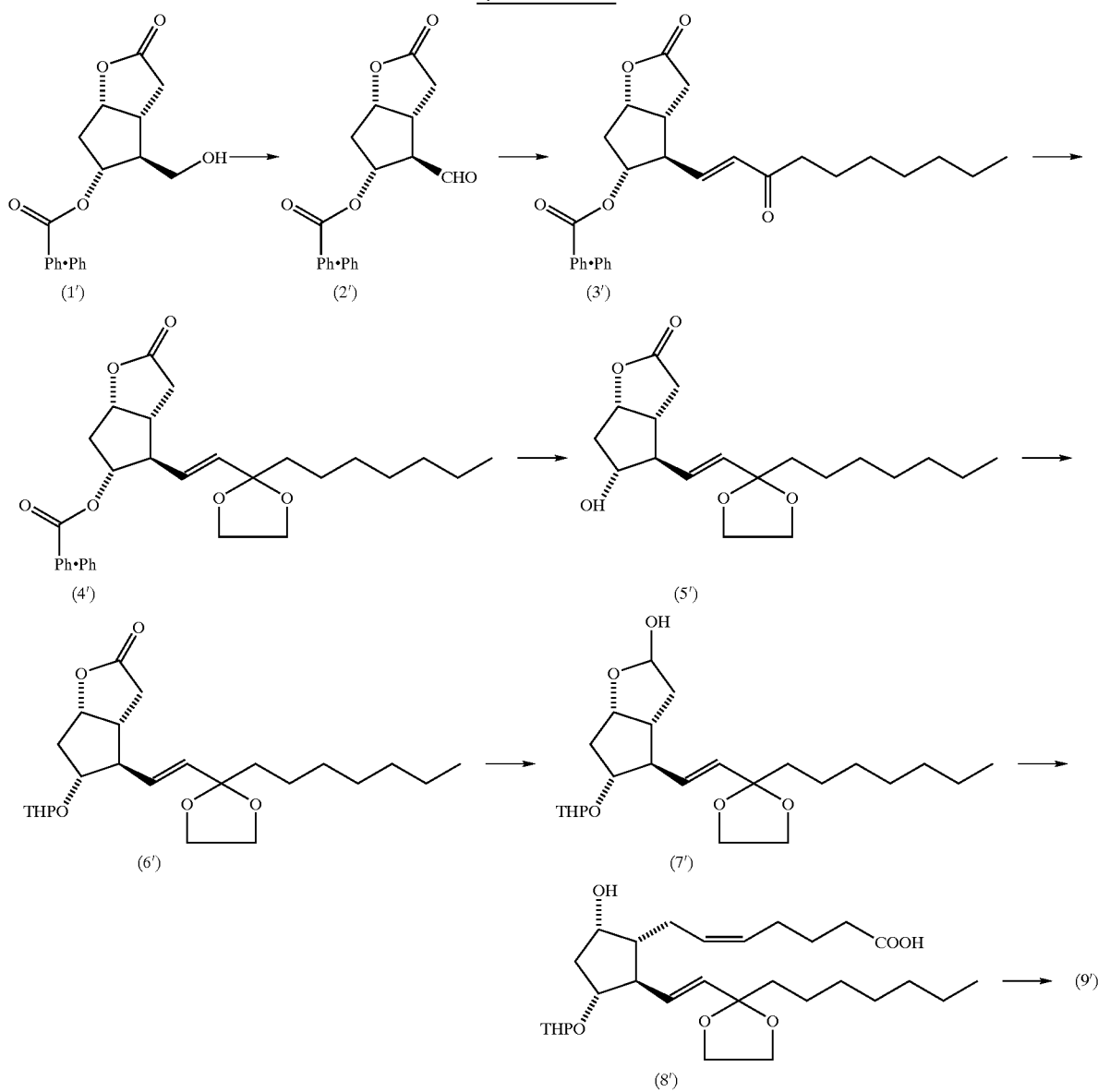
Synthetic Chart II-2
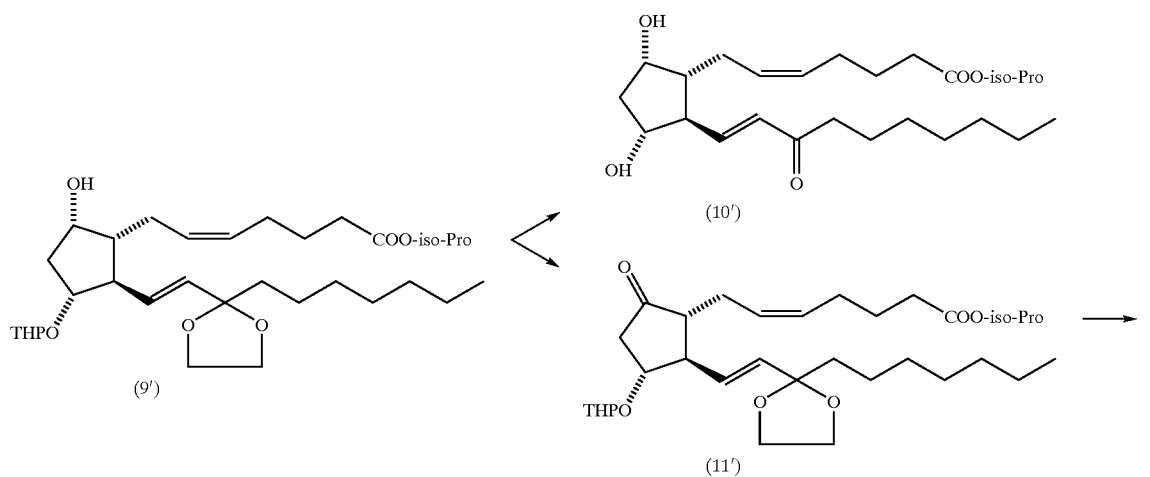

-continued
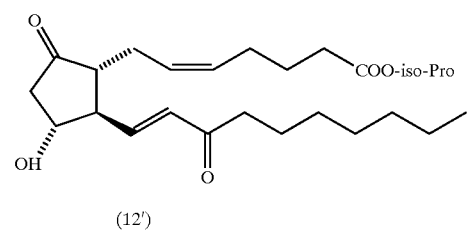
(12')
Synthetic Chart III
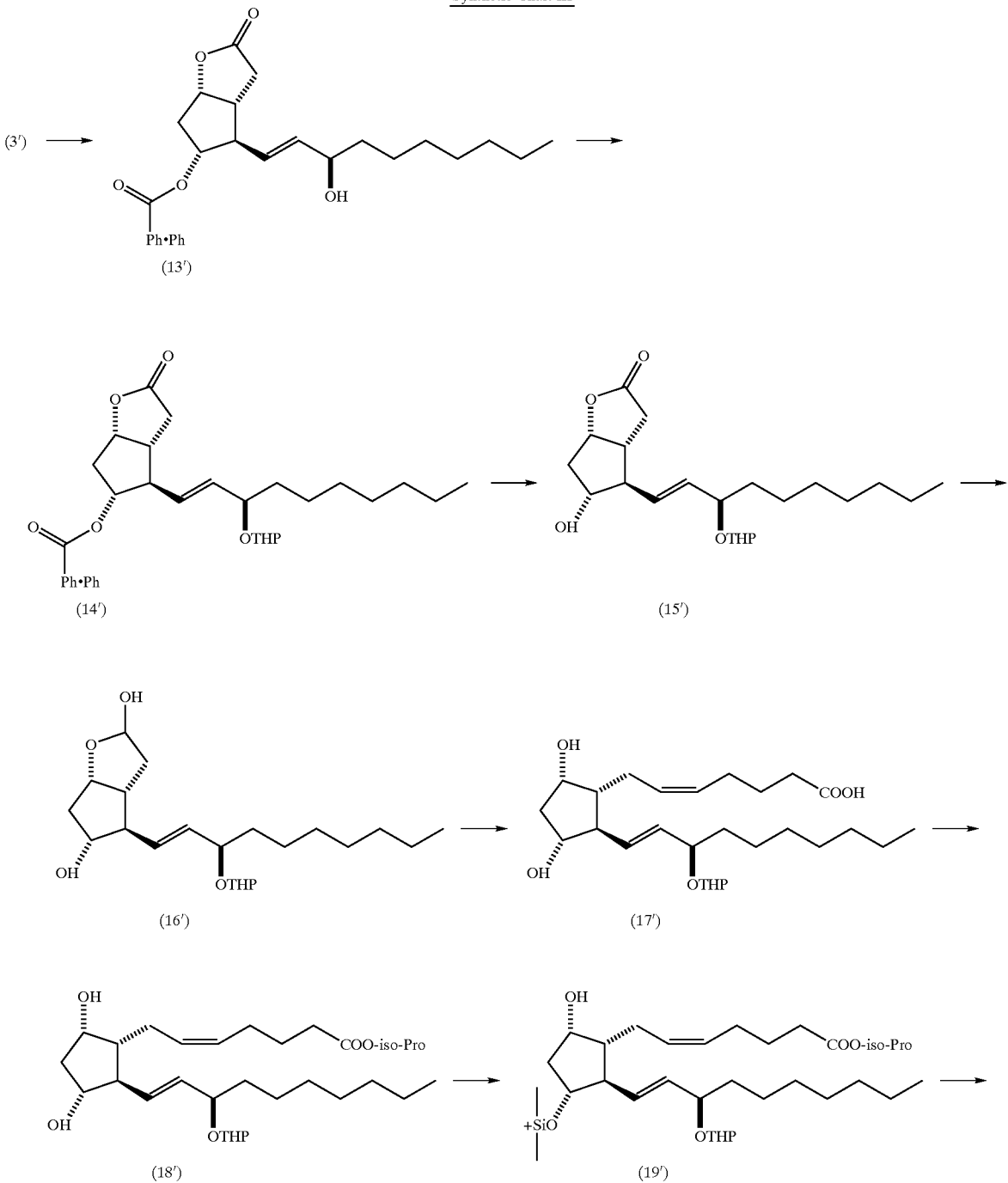

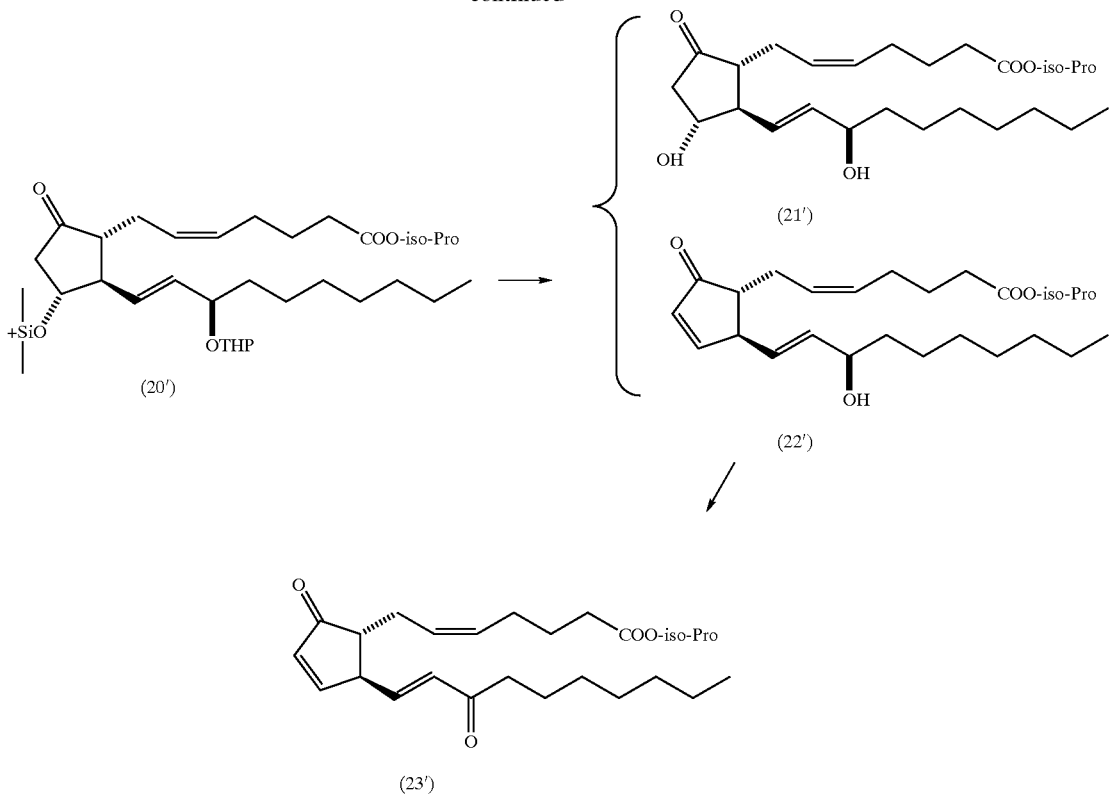

Additional Preparations

Preparations of 13,14-Dihydro-15-keto-20-ethyl-PGA$_2$ Isopropyl Ester, 13,14-Dihydro-15-keto-20-ethyl-PGE$_2$ Isopropyl Ester and 13,14-Dihydro-15-keto-20-ethyl-PGF$_2\alpha$ Isopropyl Ester (cf. Preparation Chart I)

1) Preparation of 1S-2-oxa-3-oxo-6R-(3-oxo-1-trans-decenyl)-7R-(4-phenylbenzoyloxy)-cis-bicyclo[3.3.0]-octane (3)

Commercially available (−)-Corey lactone (1) (7 g) was subjected to Collins oxidation in dichloromethane to give aldehyde (2). The resultant was allowed to react with dimethyl (2-oxononyl)phosphonate (4.97 g) anion to give 1S-2-oxa-3-oxo-6R-(3,3-ethylendioxy-1-trans-decenyl)-7R-(4-phenylbenzoyloxy)-cis-bicyclo[3.3.0]-octane (3).

2) Preparation of 1S-2-oxa-3-oxo-6R-(3-oxodecyl)-7R-(4-phenylbenzoyloxy)-cis-bicyclo[3.3.0]-octane (4)

Unsaturated ketone (3) (7.80 g) was reduced in ethyl acetate (170 ml) using 5% Pd/C under hydrogen atmosphere. The product obtained after the usual work-up (4) was used in the following reaction.

3) Preparation of 1S-2-oxa-3-oxo-6R-(3,3-ethylenedioxy-decyl)-7R-(4-phenylbenzoyloxy)-cis-bicyclo[3.3.0]-octane (5)

Saturated ketone (4) was converted to ketal (5) in dry benzene (150 ml) using ethylene glycol and p-toluenesulfonic acid (catalytic amount).

4) Preparation of 1S-2-oxa-3-oxo-6R-(3,3-ethylenedioxy-decyl)-7R-hydroxy-cis-bicyclo[3.3.0]-octane (6)

To a solution of ketal (5) in absolute methanol (150 ml) was added potassium carbonate (2.73 g). The mixture was stirred overnight at room temperature. After neutralization with acetic acid, the resultant was concentrated under reduced pressure. The resulting crude product was extracted with ethyl acetate. The organic layer was washed with a dilute aqueous solution of sodium bicarbonate and a saline, and dried. The crude product obtained after evapolation was chromatographed to give alcohol (6). Yield; 3.31 g 5) Preparation of Lactol (7)

Alcohol (6) (0.80 g) was reduced in dry toluene (8 ml) using DIBAL-H at −78° C. to give lactol (7).

6) Preparation of 13,14-Dihydro-15,15-ethylenedioxy-20-ethyl-PGF2α (8)

A DMSO solution of lactol (7) was added to ylide prepared from (4-carboxybutyl)triphenylphosphonium bromide (3.65 g). The reaction mixture was stirred overnight to give carboxylic acid (8).

7) Preparation of 13,14-dihydro-15,15-ethylenedioxy-20-ethyl-PGF$_2\alpha$ Isopropyl Ester (9)

Carboxylic acid (8) was converted to 13,14-dihydro-15, 15-ethylenedioxy-20-ethyl-PGF$_2\alpha$ isopropyl ester (9) using DBU and isopropyl iodide in acetonitrile.

Yield; 0.71 g

8) Preparation of 13,14-Dihydro-15-keto-20-ethyl-PGF$_2\alpha$ Isopropyl Ester (10)

13,14-Dihydro-15,15-ethylenedioxy-20-ethyl-PGF$_2\alpha$ isopropyl ester (9) (0.71 g) was kept in acetic acid/THF/water (3/1/1) at 40° C. for 3 hours. The crude product obtained after concentration under reduced pressure was chromatographed to give 13,14-dihydro-15-keto-20-ethyl-PGF$_2\alpha$ Isopropyl Ester (10).

Yield; 0.554 g

9) Preparation of 13,14-Dihydro-15-keto-20-ethyl-PGA$_2\alpha$ Isopropyl Ester (12)

A solution of 13,14-dihydro-15-keto-20-ethyl-PGF$_2\alpha$ isopropyl ester (10) (0.125 9) and p-toluenesulfonyl chloride (0.112 g) in pyridine (5 ml) was maintained at 0° C. for 2 days. According to the usual work-up, tosylate (11) was obtained.

Tosylate (11) was subjected to Jones oxidation in acetone (8 ml) at −25° C. The crude product obtained after the usual work-up was chromatographed to give 13,14-dihydro-15-keto-20-ethyl-PGA$_2\alpha$ isopropyl ester (2).

Yield; 0.060 g

10) Preparation of 13,14-dihydro-15,15-ethylenedioxy-20-ethyl-11-t-butyldimethylsiloxy-PGF$_2\alpha$ Isopropyl Ester (13)

13,14-Dihydro-15,15-ethylenedioxy-20-ethyl-PGF$_2\alpha$ isopropyl ester (9) (3.051 g) was dissolved in dry N,N-dimethylformamide (25 ml), t-butyldimethylsilyl chloride (1.088 g) and imidazole (0.49 g) was added thereto. The resultant was stirred at room temperature overnight. The reaction mixture was concentrated under reduced pressure, and the resulting crude product was chromatographed to give 13,14-dihydro-15,15-ethylenedioxy-20-ethyl-11-t-butyldimethylsiloxy-PGF$_2\alpha$ isopropyl ester (13).

Yield; 2.641 g

11) Preparation of 13,14-Dihydro-15,15-ethylenedioxy-20-ethyl-11-t-butyldimethylsiloxy-PGE$_2$ Isopropyl Ester (14)

13,14-Dihydro-15,15-ethylenedioxy-20-ethyl-11-t-butyldimethylsiloxy-PGF$_2\alpha$ isopropyl ester (13) (1.257 g) was subjected to Jones oxidation at −40° C. After the usual work-up, the resulting crude product was chromatographed to give 13,14-dihydro-15,15-ethylenedioxy-20-ethyl-11-t-butyldimethylsiloxy-PGE$_2$ isopropyl ester (14).

Yield; 1.082 g

12) Preparation of 13,14-Dihydro-15-keto-20-ethyl-PGE$_2$ Isopropyl Ester (15)

To a solution of 13,14-dihydro-15,15-ethylene-dioxy-20-ethyl-11-t-butyldimethylsiloxy-PGE$_2$ isopropyl ester (14) in acetonitrile was added hydrofluoric acid (46% aqueous solution). The mixture was stirred at room temperature for 40 minutes. The crude products obtained after usual work-up was chromatographed to give 13,14-dihydro-15-keto-20-ethyl-PGE$_2$ isopropyl ester (15).

Yield; 0.063 g (97%)

Preparation Chart
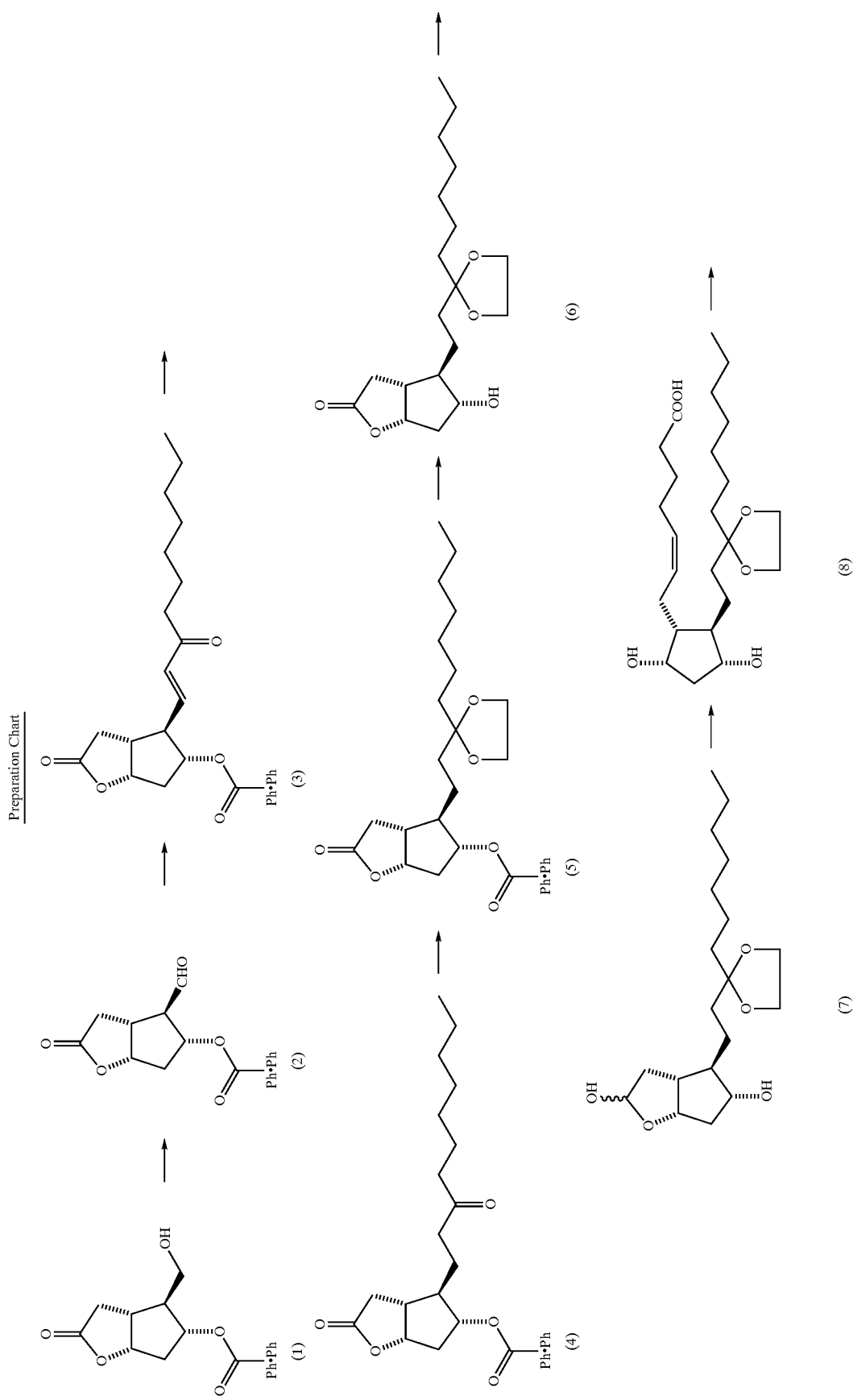

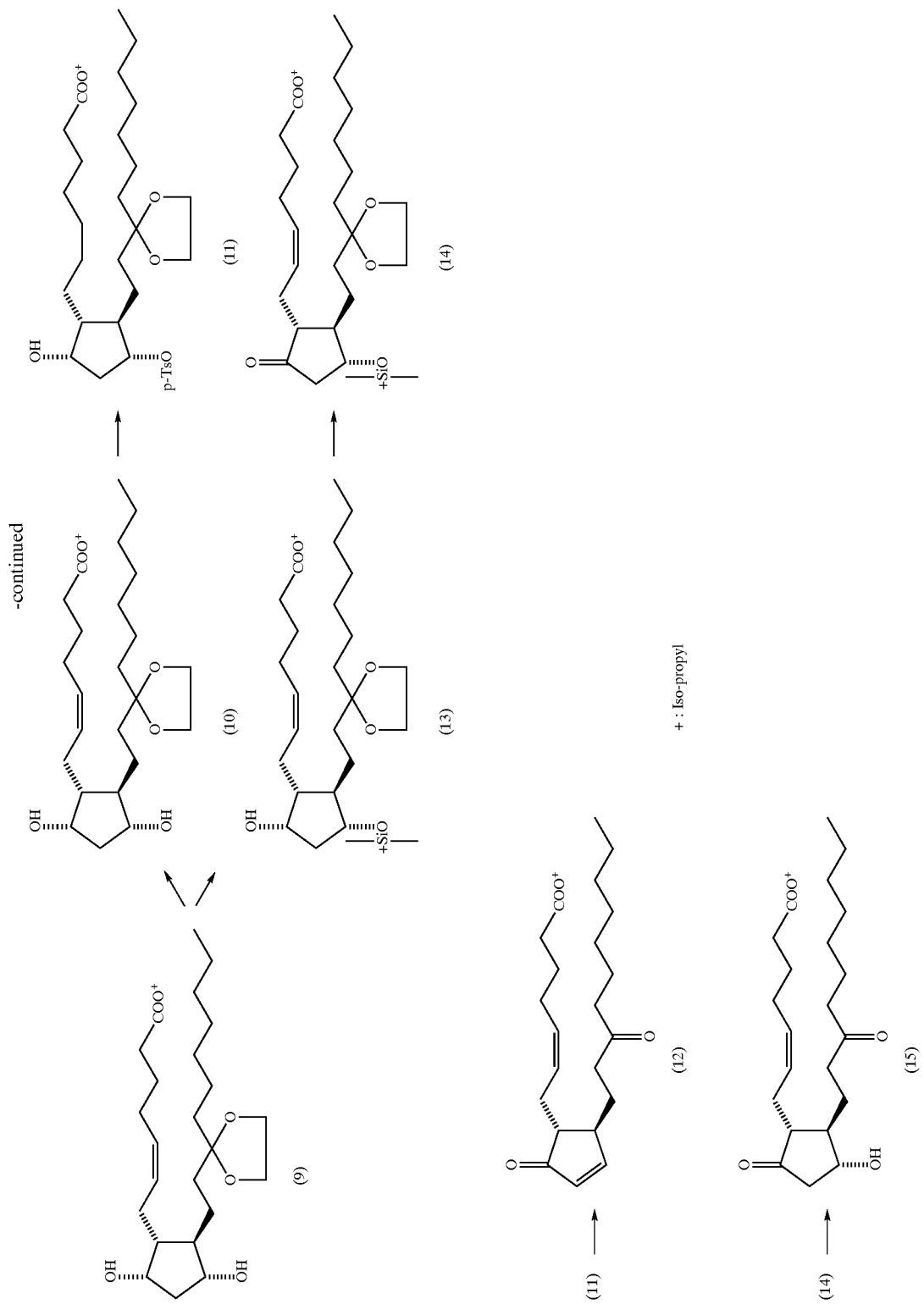

EXAMPLE 4

For the purpose of tonometry, Japanese White male rabbits (2.5–3.0 Kg) were fixed on braces, and after topical anesthetization with 0.4% oxybuprocaine hydrochloride, intraocular pressure was measured using a pheumatic applanation tonometer (manufactured by Japan Alcon K.K.).

The test drugs were suspended in a physiological saline. A 50 µl aliquot of 50 µl of the suspension (25 µg/eye of the test drug) was topically applied to one eye. The contralateral control eye received physiological saline. Intraocular pressure was measured at every 1 hr, until 6 hr, after topical application. In this experiment, 6 rabbits per group were used, and the mean values of intraocular pressure of the treated eye at each time were calculated. The results are shown in FIG. 1.

Test drugs:

(1) 13,14-dihydro-15-keto-PGD$_2$; (○ - - - ○)
(2) PGE$_2$; (● - - - ●)

As is obvious from the results, 13,14-dihydro-15-keto-PGs including 13,14-dihydro-15-keto-PGE$_2$ and the like are proved to possess ocular hypotensive potency without transient ocular hypertensive response that PGs including PGE$_2$ possess.

EXAMPLE 5

For the purpose of tonometry, Japanese White male rabbits (2.5–3.0 Kg) were fixed on braces. After topical anesthetization with 0.4% oxybuprocaine hydrochloride, intraocular pressure was measured using a pheumatic applanation tonometer (manufactured by Japan Alcon). After the topical application of 50 µl of the suspensions of the test drugs in a physiological saline to one eye, the intraocular pressure was measured and the intraocular pressure reduction (%) caused by each test drug was calculated. At the same time, the extent of conjunctival hyperemia was observed. The results are shown in Table 1.

The extent of conjunctival hyperemia:

−: scarcely observed
±: extremely weak hyperemia
+: slight hyperemia
++: pronounced hyperemia
+++: severe hyperemia

TABLE 1 (1)

| Test Drug | Dose (µg/eye) | Percent change of IOP | Hyperemia |
|---|---|---|---|
| (1) | 100 | 22 | + |
| (2) | 100 | 26 | + |
| (3) | 100 | 24 | + |
| (4) | 100 | 30 | + |
| (5) | 100 | 31 | − |
| (6) | 100 | 33 | − |
| (7) | 50 | 23 | − |

TABLE 1 (1)-continued

| Test Drug | Dose (µg/eye) | Percent change of IOP | Hyperemia |
|---|---|---|---|
| (8) | 50 | 27 | − |
| (9) | 100 | 40 | ++ |

Test drugs:
(1) 13,14-dihydro-15-keto-PGA$_1$ methyl ester
(2) 13,14-dihydro-15-keto-PGA$_1$ isopropyl ester
(3) 13,14-dihydro-15-keto-PGA$_2$ ethyl ester
(4) 13,14-dihydro-15-keto-PGA$_2$ isopropyl ester
(5) 13,14-dihydro-15-keto-20-ethyl-PGA$_1$ methyl ester
(6) 13,14-dihydro-15-keto-20-ethyl-PGA$_1$ isopropyl ester
(7) 13,14-dihydro-15-keto-20-ethyl-PGA$_2$ methyl ester
(8) 13,14-dihydro-15-keto-20-ethyl-PGA$_2$ isopropyl ester
(9) PGA$_2$

TABLE 1 (2)

| Test Drug | Dose (µg/eye) | Percent change of IOP | Hyperemia |
|---|---|---|---|
| (10) | 250 | 7 | + |
| (11) | 250 | 10 | + |
| (12) | 250 | 15 | + |
| (13) | 250 | 20 | + |
| (14) | 250 | 21 | − |
| (15) | 250 | 23 | − |
| (16) | 100 | 18 | − |
| (17) | 100 | 20 | − |
| (18) | 250 | 25 | ++ |

Test drugs:
(10) 13,14-dihydro-15-keto-PGB$_1$ methyl ester
(11) 13,14-dihydro-15-keto-PGB$_1$ isopropyl ester
(12) 13,14-dihydro-15-keto-PGB$_2$ methyl ester
(13) 13,14-dihydro-15-keto-PGB$_2$ isopropyl ester
(14) 13,14-dihydro-15-keto-20-ethyl-PGB$_1$ methyl ester
(15) 13,14-dihydro-15-keto-20-ethyl-PGB$_1$ isopropyl ester
(16) 13,14-dihydro-15-keto-20-ethyl-PGB$_2$ methyl ester
(17) 13,14-dihydro-15-keto-20-ethyl-PGB$_2$ isopropyl ester
(18) PGB$_2$

TABLE 1 (3)

| Test Drug | Dose (µg/eye) | Percent change of IOP | Hyperemia |
|---|---|---|---|
| (19) | 250 | 8 | + |
| (20) | 250 | 11 | + |
| (21) | 250 | 18 | + |
| (22) | 250 | 20 | + |
| (23) | 250 | 20 | − |
| (24) | 250 | 22 | − |
| (25) | 100 | 21 | − |
| (26) | 100 | 25 | − |
| (27) | 250 | 23 | ++ |

Test drugs:
(19) 13,14-dihydro-15-keto-PGC$_1$ methyl ester
(20) 13,14-dihydro-15-keto-PGC$_1$ isopropyl ester
(21) 13,14-dihydro-15-keto-PGC$_2$ methyl ester
(22) 13,14-dihydro-15-keto-PGC$_2$ isopropyl ester
(23) 13,14-dihydro-15-keto-20-ethyl-PGC$_1$ methyl ester
(24) 13,14-dihydro-15-keto-20-ethyl-PGC$_1$ isopropyl ester
(25) 13,14-dihydro-15-keto-20-ethyl-PGC$_2$ methyl ester
(26) 13,14-dihydro-15-keto-20-ethyl-PGC$_2$ isopropyl ester
(27) PGC$_2$

TABLE 1 (4)

| Test Drug | Dose (µg/eye) | Percent change of IOP | Hyperemia |
|---|---|---|---|
| (28) | 250 | 15 | ± |
| (29) | 250 | 17 | ± |

TABLE 1 (4)-continued

| Test Drug | Dose (μg/eye) | Percent change of IOP | Hyperemia |
|---|---|---|---|
| (30) | 250 | 20 | ± |
| (31) | 250 | 18 | ± |
| (32) | 250 | 21 | ± |
| (33) | 250 | 25 | ± |
| (34) | 250 | 23 | ± |
| (35) | 100 | 13 | + |
| (36) | 250 | 28 | ± |
| (37) | 250 | 30 | ± |
| (38) | 250 | 24 | ± |
| (39) | 250 | 28 | ± |
| (40) | 250 | 31 | ± |
| (41) | 100 | 18 | − |
| (42) | 100 | 20 | − |
| (43) | 100 | 25 | − |
| (44) | 100 | 23 | − |
| (45) | 100 | 20 | − |
| (46) | 250 | 28 | +++ |

Test drugs:
(28) 13,14-dihydro-15-keto-$PGD_1$ methyl ester
(29) 13,14-dihydro-15-keto-$PGD_1$ ethyl ester
(30) 13,14-dihydro-15-keto-$PGD_2$ ethyl ester
(31) 13,14-dihydro-15-keto-$PGD_2$ n-butyl ester
(32) 13,14-dihydro-15-keto-5,6-dehydro-$PGD_2$ methyl ester
(33) 13,14-dihydro-15-keto-5,6-dehydro-$9_\beta$-$PGD_2$
(34) 13,14-dihydro-15-keto-5,6-dehydro-$9_\beta$-$PGD_2$ methyl ester
(35) 13,14-dihydro-15-keto-16R,S-fluoro-$PGD_2$ methyl ester
(36) 13,14-dihydro-15-keto-16,16-dimethyl-$PGD_2$ methyl ester
(37) 13,14-dihydro-15-keto-19-methyl-$PGD_2$ methyl ester
(38) 13,14-dihydro-15-keto-20-methoxy-$PGD_2$
(39) 13,14-dihydro-15-keto-20-methoxy-$PGD_2$ n-butyl ester
(40) 13,14-dihydro-15-keto-16R,S-methyl-20-methoxy-$PGD_2$ methyl ester
(41) 13,14-dihydro-15-keto-20-ethyl-$PGD_1$ methyl ester
(42) 13,14-dihydro-15-keto-20-ethyl-$PGD_1$ ethyl ester
(43) 13,14-dihydro-15-keto-20-ethyl-$PGD_2$ methyl ester
(44) 13,14-dihydro-15-keto-20-ethyl-$PGD_2$ ethyl ester
(45) 13,14-dihydro-15-keto-20-methoxyethyl-$PGD_2$ methyl ester
(46) $PGD_2$

TABLE 1 (5)

| Test Drug | Dose (μg/eye) | Percent change of IOP | Hyperemia |
|---|---|---|---|
| (47) | 50 | 30 | + |
| (48) | 10 | 20 | + |
| (49) | 10 | 18 | + |
| (50) | 10 | 23 | + |
| (51) | 25 | 25 | ± |
| (52) | 25 | 32 | + |
| (53) | 25 | 18 | + |
| (54) | 25 | 20 | + |
| (55) | 25 | 23 | ± |
| (56) | 25 | 16 | + |
| (57) | 10 | 32 | + |
| (58) | 10 | 30 | + |
| (59) | 10 | 31 | + |
| (60) | 5 | 26 | + |
| (61) | 10 | 18 | + |
| (62) | 10 | 21 | + |
| (63) | 10 | 25 | + |
| (64) | 25 | 21 | ± |
| (65) | 25 | 19 | ± |
| (66) | 2S | 23 | ± |
| (67) | 25 | 20 | − |
| (68) | 25 | 25 | − |
| (69) | 10 | 30 | − |

TABLE 1 (5)-continued

| Test Drug | Dose (μg/eye) | Percent change of IOP | Hyperemia |
|---|---|---|---|
| (70) | 10 | 31 | − |
| (71) | 10 | 24 | − |
| (72) | 10 | 12 | − |
| (73) | 10 | 32 | +++* |

*: Lid closure and lacrimation were observed.

Test drugs:
(47) 13,14-dihydro-15-keto-$PGE_1$ ethyl ester
(48) 13,14-dihydro-6,15-diketo-$PGE_1$ ethyl ester
(49) 13,14-dihydro-6,15-diketo-$PGE_1$ n-butyl ester
(50) ±13,14-dihydro-6,15-diketo-$PGE_1$ ethyl ester
(51) 13,14-dihydro-6,15-diketo-11-dehydroxy-11R-methyl-$PGE_1$ ethyl ester
(52) 13,14-dihydro-6,15-diketo-16R,S-fluoro-11-dehydroxy-11R-methyl-$PGE_1$ ethyl ester
(53) 13,14-dihydro-6,15-diketo-16,16-dimethyl-$PGE_1$ ethyl ester
(54) 13,14-dihydro-6,15-diketo-19-methyl-$PGE_1$ methyl ester
(55) 13,14-dihydro-6,15-diketo-11-dehydroxy-11R-hydroxymethyl-$PGE_1$ methyl ester
(56) 13,14-dihydro-15-keto-$PGE_2$
(57) 13,14-dihydro-15-keto-$PGE_2$ methyl ester
(58) 13,14-dihydro-15-keto-$PGE_2$ isopropyl ester
(59) 13,14-dihydro-15-keto-$\Delta^2$-$PGE_2$ methyl ester
(60) 13,14-dihydro-15-keto-16R,S-fluoro-$PGE_2$ ethyl ester
(61) 13,14-dihydro-15-keto-3,16-dimethyl-$PGE_2$ methyl ester
(62) 13,14-dihydro-15-keto-16R,S-hydroxy-$PGE_2$ ethyl ester
(63) 13,14-dihydro-15-keto-19-methyl-$PGE_2$ ethyl ester
(64) 13,14-dihydro-15-keto-20-methoxy-$PGE_2$ methyl ester
(65) 13,14-dihydro-15-keto-20-methoxy-$\Delta^2$-$PGE_2$ methyl ester
(66) 13,14-dihydro-15-keto-16-dimethyl-20-methoxy-$PGE_2$ methyl ester
(67) 13,14-dihydro-15-keto-20-ethyl-$PGE_1$ methyl ester
(68) 13,14-dihydro-6,15-diketo-20-methyl-$PGE_1$ methyl ester
(69) 13,14-dihydro-15-keto-20-ethyl-$PGE_2$ methyl ester
(70) 13,14-dihydro-15-keto-20-ethyl-$PGE_2$ ethyl ester
(71) 13,14-dihydro-15-keto-20-n-propyl-$PGE_2$ methyl ester
(72) 13,14-dihydro-15-keto-20-ethyl-11-dehydroxy-11R-methyl-$PGE_2$ methyl ester
(73) $PGE_2$

TABLE 1 (6)

| Test Drug | Dose (μg/eye) | Percent change of IOP | Hyperemia |
|---|---|---|---|
| (74) | 100 | 28 | + |
| (75) | 100 | 22 | + |
| (76) | 100 | 33 | + |
| (77) | 100 | 38 | + |
| (78) | 20 | 25 | + |
| (79) | 10 | 42 | ± |
| (80) | 100 | 41 | + |
| (81) | 250 | 21 | + |
| (82) | 250 | 40 | + |
| (83) | 100 | 33 | ± |
| (84) | 25 | 17 | − |
| (85) | 50 | 28 | − |
| (86) | 50 | 28 | − |
| (87) | 50 | 25 | − |
| (88) | 50 | 23 | − |
| (89) | 250 | 23 | + |
| (90) | 250 | 25 | ± |
| (91) | 250 | 26 | − |
| (92) | 25 | 43 | ± |
| (93) | 10 | 26 | ± |
| (94) | 250 | 30 | − |
| (95) | 250 | 18 | − |
| (96) | 100 | 46 | +++* |

TABLE 1 (6)-continued

| Test Drug | Dose (μg/eye) | Percent change of IOP | Hyperemia |
|---|---|---|---|
| (97) | 25 | 27 | +++* |
| (98) | 25 | 31 | +++* |

*: Lid closure and lacrimation were observed.
Test drugs:
(74) 13,14-dihydro-15-keto-PGF$_1$α ethyl ester
(75) 13,14-dihydro-15-keto-PGF$_2$α methyl ester
(76) 13,14-dihydro-15-keto-PGF$_2$α ethyl ester
(77) 13,14-dihydro-15-keto-9$_β$, 11$_α$ -PGF$_2$ methyl ester
(78) 13,14-dihydro-15-keto-16R,S-fluoro-PGF$_2$α
(79) 13,14-dihydro-15-keto-16R,S-fluoro-PGF$_2$α methyl ester
(80) 13,14-dihydro-15-keto-16R,S-fluoro-11-dehydroxy-11R-methyl-PGF$_2$α methyl ester
(81) 13,14-dihydro-15-keto-16,16-dimethyl-PGF$_2$α methyl ester
(82) 13,14-dihydro-15-keto-17S-methyl-PGF$_2$α ethyl ester
(83) 13,14-dihydro-15-keto-20-ethyl-PGF$_1$α methyl ester
(84) 13,14-dihydro-15-keto-20-ethyl-PGF$_2$α
(85) 13,14-dihydro-15-keto-20-ethyl PGF$_2$α methyl ester
(86) 13,14-dihydro-15-keto-20-ethyl PGF$_2$α ethyl ester
(87) 13,14-dihydro-15-keto-20-ethyl PGF$_2$α isopropyl ester
(88) 13,14-dihydro-15-keto-20-ethyl PGF$_2$α n-butyl ester
(89) 13,14-dihydro-15-keto-20-methyl PGF$_2$α methyl ester
(90) 13,14-dihydro-15-keto-20-n-propyl-PGF$_2$α methyl ester
(91) 13,14-dihydro-15-keto-20-n-butyl-PGF$_2$α methyl ester
(92) 13,14-dihydro-15-keto-20-ethyl-16R,S-fluoro-PGF$_2$α
(93) 13,14-dihydro-15-keto-20-ethyl-16R,S-fluoro-PGF$_2$α methyl ester
(94) 13,14-dihydro-15-keto-20-ethyl-11-dehydroxy-11R-methyl-PGF$_2$α methyl ester
(95) 13,14-dihydro-15-keto-20-ethyl-16R,S-fluoro-11-dehydroxy-11R-methyl-PGF$_2$α methyl ester
(96) PGF$_2$α
(97) PGF$_2$α methyl ester
(98) PGF$_2$α isopropyl ester The n.m.r. of the above compounds used in the Example 2 and Mass are shown hereinafter:

$^1$H n.m.r. was determined using heavy chloroform as a solvent by a NMR spectrometer R-90H available from Hitachi Seisakusho.

Mass was determined by a mass spectrometer M-80B available from Hitachi Seisaku-sho;

EI method: at ionization patential of 70 eV, SIMS method: silver plate-glycerin matrix.

Compound (3)
δ: 0.88(3H, t, J=6 Hz), 1.25(3H, t, J=7 Hz), 1.10–2.75 (22H, m), 4.11(2H, q, J=7 Hz), 5.37(2H, m), 6.12(1H, dd, J=6 Hz, J=2.5Hz), 7.53(1H, dd, J=6 Hz, J=3 Hz)

Compound (8)
δ: 0.86(3H, t, J=5.5 Hz), 1.21(6H, d, J=6 Hz), 1.05–2.75 (26H, m), 4.96(1H, hept, J=6 Hz), 5.37(2H, m), 6.09(1H, dd, J=6 Hz, J=2 Hz, 7.50(1H, J=6 Hz, J=2.5 Hz) Mass(EI) m/z 404(M$^+$), 345(M$^+$-i-C$_3$H$_7$O)

Compound (30)
δ: 0.89(3H, t, J=6 Hz), 1.26(3H, t, J=7 Hz), 1.06–2.93 (25H, m), 4.13(2H, q, J=7 Hz), 4.41(1H, m), 5.47(2H, m)

Compound (34)
δ: 0.89(3H, t, J=6 Hz), 1.09–2.96(25H, m), 3.63(3H, s), 4.19(1H, m)

Compound (35)
δ: 0.91(3H, t, J=6 Hz), 1.1–2.93(23H, m), 3.64(3H, s), 4.3–4.5(1.5H, m), 4.98(0.5H, dd, J=6 Hz), 5.50(2H, m) Mass(SIMS) m/z 385(M+H)$^+$, 367(M$^+$+1-H$_2$O), 365(M$^+$+1-HF)

Compound(37)
δ: 0.86(6H, d, J=7 Hz), 0.94–2.90(24H, m), 3.64(3H, s), 4.38(1H, m), 5.43(2H, m) Mass(EI) m/z 380(M$^+$), 362(M$^+$-H$_2$O), 331, 234, 222

Compound(40)
δ: 1.05(3H, d, J=7 Hz), 0.80–2.83(24H, m), 3.28(3H, s), 3.32(2H, t, J=6 Hz), 3.64(3H, s), 4.29–4.47(1H, m), 5.44 (2H, m)

Compound(45)
δ: 1.10–2.95(29H, m), 3.30(3H, s), 3.33(2H, t, J=6 Hz), 3.66(3H, s), 4.38(1H, m), 5.44(2H, m)

Compound(55)
δ: 0.86(6H, d, J=6 Hz), 0.98–2.98(26H, m), 2.71(1H, m), 3.63(3H, S), 3.50–3.81(2H, m) Mass(EI) m/z 410(M$^+$), 392(M$^+$–18), 379, 361

Compound(58)
δ: 0.88(3H, t, J=6 Hz), 1.22(6H, d, J=6.5 Hz), 1.07–3.03 (25H, m), 4.03(1H, m), 4.97(33H, hept, J=6.5 Hz), 5.37(2H, M)

Compound(67)
δ: 0.87(3H, t, J=6 Hz), 1.03–2.84(33H, m), 3.64(3H, s), 3.98(1H, m)

Compound(68)
δ: 0.87(3H, t, J=6 Hz), 1.23(3H, t, J=7 Hz), 1.03–2.88 (29H, m), 4.08(2H, q, J=7 Hz), 3.86–4.23 (1H, m)

Compound(69)
δ: 0.88(3H, t, J=6 Hz), 1.07–2.90(29H, m), 3.64(3H, s), 4.02(1H, m), 5.35(2H, m)

Compound(70)
δ: 0.87(3H, t, J=6 Hz), 1.23(3H, t, J=7 Hz), 1.07–2.83 (29H, m), 4.08(2H, q, J=7 Hz), 3.79–4.22(1H, m), 5.34(2H, m) Mass(EI) m/z 408,390,345

Compound(71)
δ: 0.87(3H, t, J=5 Hz), 1.00–2.83(31H, m), 3.63(3H, s), 3.86–4.15(1H , m), 5.34(2H, m) Mass(SIMS) m/z 409,391, 369

Compound(72)
δ: 0.87(3H, t, J=5 Hz), 1.11(3H, d, J=6 Hz), 1.00–2.60 (29H, m), 3.63(3H, s), 5.33(2H, m) Mass(EI) m/z 392,374, 361,343

Compound(83)
δ: 0.87(3H, t, J=6 Hz), 1.15–2.70(34H, m), 3.63(3H, s), 3.86(1H, m), 4.15(1H, m) Mass(EI) m/z 398(M$^+$),380(M$^+$-18),362,349

Compound(84)
δ: 0.86(3H, t, J=6 Hz), 1.15–2.70(28H, m), 3.85(1H, m), 4.12(1H, m), 5.10–5.75($^5$H, m) Mass(EI) m/z 364(M$^+$–18), 346

Compound(85)
δ: 0.87(3H, t, J=6 Hz), 1.10–2.65(30H, m), 3.63(3H, s), 3.85(1H, m), 4.13(1H, m), 5.38(2H, m) Mass(SIMS) m/z 397(M$^+$+1), 379(M$^+$+1–H$_2$O), 361(M$^+$+1–2H$_2$O), 345,330

Compound(86)
δ: 0.87(3H, t, J=6 Hz), 1.24(3H, t, J=7 Hz), 1.10–2.95 (30H, m), 3.85(1H, m), 4.08(2H, q, J=7 Hz), 3.93–4.25(1H, m), 5.38(2H, m) Mass(EI) m/z 410(M$^+$),392(M$^+$–18),374

Compound(87)
δ: 0.87(3H, t, J=6 Hz), 1.22(6H, d, J=6.5 Hz), 1.10–2.75 (30H, m), 3.85(1H, m), 4.13(1H, m), 4.95(1H, hept, J=6.5 Hz), 5.38(2H, m) Mass(EI) m/z 424(M$^+$),406(M$^+$–18),388, 347

Compound(88)
δ: 0.70–1.03(6H, m), 1.10–3.05(34H, m), 3.84(1H, m), 4.03(2H, t, J=6.5 Hz), 4.10(1H, m), 5.38(2H, m) Mass(EI) m/z 420(M$^+$),402(M$^+$–18),376,347

Compound(89)
δ: 0.87(3H, t, J=6 Hz), 1.15–2.70(28H, m), 3.62(3H, s), 3.83(1H, m), 4.12(1H, m), 5.37(2H, m) Mass(SIMS) m/z 383(M$^+$1), 365(M$^+$+1-18), 347

Compound (90)
δ: 0.87(3H, t, J=6 Hz), 1.10–2.70(32H, m), 3.63(3H, s), 3.85(1H, m), 4.12(1H, m), 5.38(2H, m)

Compound(91)
δ: 0.87(3H, t, J=6 Hz), 1.10–2.70(34H, m), 3.63(3H, s), 3.83(1H, m), 4.12(1H, m), 5.38(2H, m)

Compound(92)

δ: 0.87(3H, t, J=6 Hz), 1.10–2.90 (26H, m)., 3.87(1H, m), 4.12(1H, m), 4.43(0.5H, m), 4.50–5.10(3H, brs),4.99(0.5H, m), 5.38(2H, m) Mass(EI) m/z 400($M^+$), 382($M^+$), 382($M^+$-18),362,344

Compound(94)

δ: 0.87(3H, t, J=5.5 Hz), 1.06(3H, d, J=6 Hz), 1.15–2.55 (30H, m), 3.63(3H, s), 4.08(1H, m), 5.38(2H, m) Mass(EI) m/z 394($M^+$), 375($M^+$-18), 358,344

Compound(95)

δ: 0.88(3H, t, J=6 Hz), 1.08(3H, d, J=6 Hz), 1.15–2.75 (28H, m), 3.63(3H, s), 4.09(1H, m), 4.42(0.5H, m), 4.97 (0.5H, m), 5.38(2H, m) Mass(EI) m/z 412($M^+$), 394($M^+$-18)

EXAMPLE 6

For the purpose of tonometry, Japanes White male rabbits (2.5 Kg–3.0 Kg) were fixed on braces. After anesthetization by topical application of 0.4% oxybuprocaine hydrochloride, the intraocular pressure was determined using a pneumatic applanation tonometer (manufactured by Japan Alcon K.K.).

The test drugs were suspended in a physiological saline, and a 50 μl aliquot (25 μg/eye of the test drug) was topically applied to one eye, while the other eye received physiological saline. At every 0.5 hr after topical application, up to 2 hr, the intraocular pressure was measured and side effects were observed and assessed. In this experiment, 6 rabbits per group were used, and mean value of the intraocular pressure of the treated eye (the change (mmHg) provided that the intraocular pressure at 0 hr is 0) and rating of the assessment of the side effects at each time were determined. The side effects were rated according to the following standard.

The results are shown in Tables 2 and 3.

TABLE 2

(Charge in intraocular pressure; Means ± S.E. mmHg)

| Test Drug | Time (hr) | | | |
|---|---|---|---|---|
| | 0.5 | 1.0 | 1.5 | 2.0 |
| 1 | −1.7 ± 0.5 | −3.4 ± 1.0 | −2.5 ± 1.4 | −1.2 ± 1.8 |
| 4 | +4.0 ± 1.1 | +0.8 ± 1.4 | +0.5 ± 1.0 | −0.5 ± 1.9 |
| 2 | −2.9 ± 0.7 | −5.4 ± 1.5 | −6.4 ± 1.1 | −6.3 ± 1.1 |
| 5 | +5.3 ± 0.8 | +10.3 ± 0.4 | +5.4 ± 1.4 | +0.2 ± 1.4 |
| 3 | −2.3 ± 1.0 | −4.3 ± 1.9 | −4.8 ± 1.1 | −4.8 ± 0.7 |
| 6 | +2.2 ± 1.1 | +3.8 ± 2.5 | +1.5± 1.9 | −1.0 ± 1.8 |

TABLE 3

(Evaluation of side effects)

| Test Drug | Time (hr) | | | |
|---|---|---|---|---|
| | 0.5 | 1.0 | 1.5 | 2.0 |
| 1 | 2.2 ± 0.2 | 2.0 ± 0.3 | 1.5 ± 0.2 | 1.2 ± 0.4 |
| 4 | 3.2 ± 0.4 | 3.0 ± 0.6 | 2.8 ± 0.5 | 2.5 ± 0.3 |
| 2 | 2.8 ± 0.3 | 3.1 ± 0.3 | 2.7 ± 0.4 | 2.2 ± 0.5 |
| 5 | 5.0 ± 0.0 | 5.2 0.2 | 5.0 ± 0.0 | 4.8 ± 0.2 |
| 3 | 2.0 ± 0.4 | 2.3 ± 0.6 | 2.0 ± 0.5 | 1.7 ± 0.7 |
| 6 | 5.0 ± 0.0 | 5.2 ± 0.2 | 5.3 ± 0.2 | 5.3 ± 0.3 |

Standard of the evaluation of the side effects (ocular response)

| Scale for Scoring Ocular Lesions | |
|---|---|
| 1) Cornea | |
| A) Opacity-degree of density (area most dense taken for reading) | |
| No Opacity | 0 |
| Scattered or diffuse area, details of iris clearly visible | 1 |
| Easily discernible translucent areas, details of iris slightly obscured | 2 |
| Opalescent areas, no details of iris visible, size of pupil barely discernible | 3 |
| Opaque, iris invisible | 4 |
| B) Area of cornea involved | |
| One quarter (or less) but not zero | 1 |
| Greater than one quarter, but less than half | 2 |
| Greater than half, but less than three quarters | 3 |
| Greater than three quarters, up to whole area | 4 |
| A × B × 5 | Total maximum = 80 |
| 2) Iris | |
| A) Values | |
| Normal | 0 |
| Folds above normal, congestion, swelling, circumcorneal injection (any or all of these or combination of any thereof) iris still reacting to light (sluggish reaction is positive) | 1 |
| No reaction to light, hemorrhage, gross destruction (any or all of these) | 2 |
| A × 5 | Total maximum = 10 |
| 3) Conjunctivae | |
| A) Redness (refers to palpebral and bulbar conjunctivae excluding cornea and iris) | |
| Vessels normal | 0 |
| Vessels definitely injected above normal | 1 |
| More diffuse, deeper crimson red, individual vessels not easily discemible | 2 |
| Diffuse beefy red | 3 |
| B) Chemosis | |
| No swelling | 0 |
| Any swelling above normal (includes nictitating membrane) | 1 |
| Obvious swelling with partial eversion of lids | 2 |
| Swelling with lids about half closed | 3 |
| Swelling with lids about half closed to completely closed | 4 |
| C) Discharge | |
| No discharge | 0 |
| Any amount different from normal (dose not include small amounts observed in inner canthus of normal animals) | 1 |
| Discharge with moistening of the lids and hairs just adjacent to lids | 2 |
| Discharge with moistening of the lids and hairs, and considerable area around the eye | 3 |
| Score (A' + B + C) × 2 | Total maximum = 20 |

Test Drugs 1. 13,14-dihydro–15-keto–20-ethyl-$PGF_2α$
2. 13,14-dihydro–15-keto–20-ethyl-$PGF_2α$ methyl ester
3. 13,14-dihydro–15-keto–20-ethyl-$PGF_2α$ isopropyl ester
4. $PGF_2α$
5. $PGF_2α$ methyl ester
6. $PGF_2α$ isopropyl ester As is obvious from above results, 13,14-dihydro–15-keto–20-alkyl-PGs including 13,14-dihydro–15-keto–20-ethyl-$PGF_2$s cause intraocular pressure reduction without transient ocular hypertensive response connected with PGs including PGF$_2$s. Esters are proved to have a stronger tendency to cause intraocular pressure reduction than carboxyl acid type. Compared with PGs including PGF$_2$s, 13,14-dihydro-15-keto-20-alkyl-PGs including 13,14-dihydro-15-keto-20-ethyl-PGF$_2$s are accompanied with extremely reduced side effects, which are hardly detectable.

EXAMPLE 7

For the purpose of tonometry, Japanese White male rabbits (2.5 Kg–3.0 Kg) were fixed on braces. After anesthetization by topical application of 0.4% oxybuprocaine hydrochloride, the intraocular pressure was determined using on a pneumatic applanation tonometer (manufactured by Japan Alcon K.K.).

The test drugs were suspended in a physiological saline, and a 50 μl aliquot (25 μg/eye of the test drug) was topically applied to one eye, while the other eye received physiological saline. At every 1 hr after topical application, up to 4 hr, the intraocular pressure was measured.

The results are shown in Table 4

TABLE 4

| Test Drug | Time 0 | 1 | 2 | 3 | 4 |
|---|---|---|---|---|---|
| 1 | 21.3 ± 3.6[1] | 29.3 ± 3.5 (+37.6)[2] | 22.0 ± 3.4 (+3.3) | 19.8 ± 1.5 (−7.0) | 18.5 ± 1.9 (−13.1) |
| 2 | 17.7 ± 1.5 | 14.3 ± 1.5 (−19.2) | 12.7 ± 3.2 (−28.2) | 12.3 ± 2.9 (−30.5) | 14.3 ± 3.8 (−19.2) |

Test Drugs:
1. PGE$_2$
2. 13,14-dihydro-15-keto-20-ethyl-PGE$_2$ isopropyl ester
[1] Mean ± S.E. of intraocular pressure (mmHg)
[2] Percent change of intraocular pressure (%)

What is claimed is:
1. A pharmaceutical composition for treatment of glaucoma which comprises a glaucoma treating effective amount of a prostaglandin compound of the formula

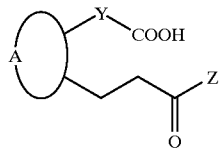

wherein, A is

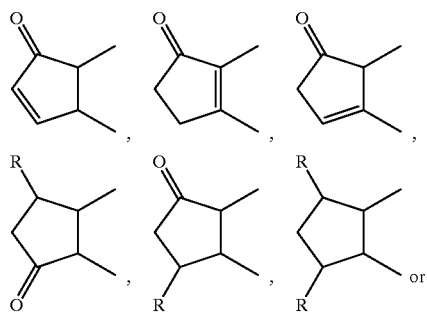

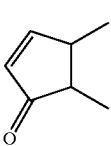

wherein R is hydroxyl, hydroxylalkyl or alkyl; Y is a saturated or unsaturated C$_{2-6}$ hydrocarbon chain; or a physiologically acceptable salt or esterified carboxyl group derivative selected from the group consisting of C$_{1-8}$ alkyl, C$_{3-6}$ cycloalkyl, benzyl, phenyl, hydroxy C$_{1-3}$ alkyl, C$_{1-2}$ alkoxy C$_{1-3}$ alkyl, tri-C$_{1-2}$ alkylsilyl and tetrahydropyranyl; and

comprises

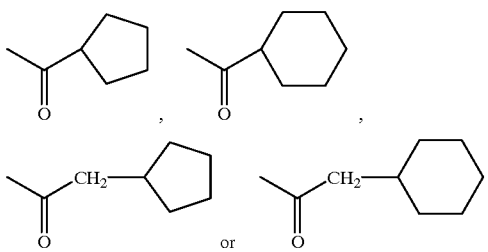

2. A pharmaceutical composition for treatment of ocular hypertension which comprises an ocular hypertension treating effective amount of a prostaglandin compound of the formula

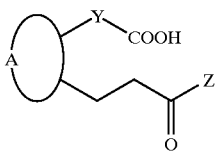

wherein, A is

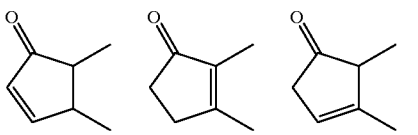

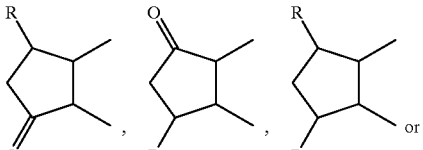

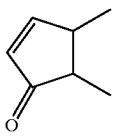

wherein R is hydroxyl, hydroxylalkyl or alkyl; Y is a saturated or unsaturated $C_{2-6}$ hydrocarbon chain; or a physiologically acceptable salt or esterified carboxyl group derivative selected from the group consisting of $C_{1-8}$ alkyl, $C_{3-6}$ cycloalkyl, benzyl, phenyl, hydroxy $C_{1-3}$ alkyl, $C_{1-2}$ alkoxy $C_{1-3}$ alkyl, tri-$C_{1-2}$ alkylsilyl and tetrahydropyranyl; and
comprises
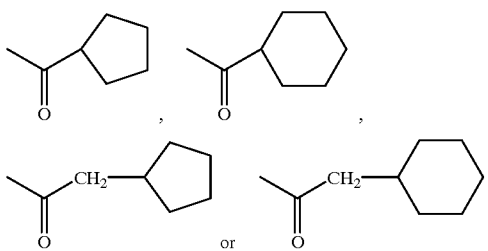
* * * * *

UNITED STATES PATENT AND TRADEMARK OFFICE
CERTIFICATE OF CORRECTION

PATENT NO.     : 6,420,422 B1
DATED          : July 16, 2002
INVENTOR(S)    : Ryuji Ueno It is certified that error appears in the above-identified patent and that said Letters Patent is hereby corrected as shown below:

<u>Title page,</u>
Item [73], Assignee, delete "Sucampo Pharmaceuticals, Inc., Bethesda, MD (US)" and insert therefor -- R-Tech Ueno, Ltd., Osaka (JP) --.

Item [75], Inventors, delete "Ryuzo Ueno; Ryuji Ueno, both of Nishinomiya; Tomio Oda, Sanda, all of (JP)" and insert therefor -- Ryuji Ueno, Nishinomiya (JP) --.

Signed and Sealed this

Twenty-ninth Day of April, 2003

JAMES E. ROGAN
*Director of the United States Patent and Trademark Office*